United States Patent
Li et al.

(10) Patent No.: US 11,670,424 B2
(45) Date of Patent: Jun. 6, 2023

(54) EVALUATION OF REDUCTION OF DISEASE RISK AND TREATMENT DECISION

(71) Applicant: INTERNATIONAL BUSINESS MACHINES CORPORATION, Armonk, NY (US)

(72) Inventors: Jing Li, Beijing (CN); Jing Mei, Beijing (CN); Yi Qin Yu, Beijing (CN); Jian Wang, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 310 days.

(21) Appl. No.: 17/031,592

(22) Filed: Sep. 24, 2020

(65) Prior Publication Data

US 2022/0093259 A1 Mar. 24, 2022

(51) Int. Cl.
*G16H 50/30* (2018.01)
*G16H 10/60* (2018.01)
(Continued)

(52) U.S. Cl.
CPC ........... *G16H 50/30* (2018.01); *A61B 5/7275* (2013.01); *G06F 16/2246* (2019.01);
(Continued)

(58) Field of Classification Search
CPC ........ G16H 50/30; G16H 10/40; G16H 10/60; G16H 50/70; G16H 50/20; G16H 70/20;
(Continued)

(56) References Cited

U.S. PATENT DOCUMENTS

| 2002/0184050 A1 | 12/2002 | Papageorge |
| 2010/0204920 A1 | 8/2010 | Dranitsaris |

(Continued)

FOREIGN PATENT DOCUMENTS

| CN | 101236554 A | 8/2008 |
| CN | 103970792 A | 8/2014 |
| CN | 105653554 A | 6/2016 |

OTHER PUBLICATIONS

United Kingdom Intellectual Property Office, Combined Search Report under Section 17(5)(b) and Abbreviated Examination Report under Section 18(3), Application No. GB2113144.6, dated Jan. 19, 2022, 6 pgs.

(Continued)

*Primary Examiner* — Michael Tomaszewski
*Assistant Examiner* — Rachael Sojin Stone
(74) *Attorney, Agent, or Firm* — Caleb D. Wilkes

(57) ABSTRACT

A method, a system and a computer program product may evaluate reduction of disease risk. Patient data of a patient may be received. A selection of a disease outcome may be received. A risk score that the patient will experience the selected disease outcome may be determined. The determining may use the patient data. Intervention options may be generated based on the patient data and by accessing a medical record data structure. An intervention effect for each of the intervention options may be determined. The intervention effect may change the risk score. The intervention effects may be compared. A recommendation of at least one of the intervention options may be provided based on the comparing of the intervention effects.

25 Claims, 8 Drawing Sheets

(51) Int. Cl.
    *G16H 50/20*     (2018.01)
    *G16H 70/20*     (2018.01)
    *G16H 10/40*     (2018.01)
    *G16H 50/70*     (2018.01)
    *A61B 5/00*     (2006.01)
    *G06F 16/22*     (2019.01)
    *G06F 16/28*     (2019.01)

(52) U.S. Cl.
CPC ........... *G06F 16/288* (2019.01); *G16H 10/40* (2018.01); *G16H 10/60* (2018.01); *G16H 50/20* (2018.01); *G16H 50/70* (2018.01); *G16H 70/20* (2018.01)

(58) Field of Classification Search
CPC .. G06F 16/2246; G06F 16/288; A61B 5/7275
USPC ............................................................ 705/3
See application file for complete search history.

(56) References Cited

U.S. PATENT DOCUMENTS

2020/0251213 A1*   8/2020   Tran ...................... G06N 20/00
2022/0384045 A1*   12/2022   Zimmerman .......... G16H 50/20

OTHER PUBLICATIONS

IBM, Response to United Kingdom Intellectual Property Office's Examination Report dated Jan. 19, 2022, Mar. 31, 2022, 4 pgs., GB Application No. 2113144.6.

Borenstein et al., "A basic introduction to fixed-effect and random-effects models for meta-analysis," Research Synthesis Methods, 2010, vol. 1, pp. 97-111, (wileyonlinelibrary.com) DOI: 10.1002/jrsm.12.

Denig et al., "The effect of a patient-oriented treatment decision aid for risk factor management in patients with diabetes (PORTDA-diab): study protocol for a randomised controlled trial," Trials, 2012, 13:219, http://www.trialsjournal.com/content/13/1/219, 12 pages.

Kanwar et al., "The Use of Risk Assessment Tools and Prognostic Scores in Managing Patients with Pulmonary Arterial Hypertension," Curr Hypertens Rep., 21(6): 45, Sep. 23, 2019, doi:10.1007/s11906-019-0950-y, 26 pages.

Karmali et al., "Global Risk Assessment to Guide Blood Pressure Management in Cardiovascular Disease Prevention," Hypertension, Mar. 2017, pp. e2-e9, vol. 69 Issue 3, DOI: 10.1161/HYPERTENSIONAHA.116.08249, downloaded on Jan. 2, 2020 from https://www.ahajournals.org/doi/epub/10.1161/HYPERTENSIONAHA.116.08249.

Karmali et al., "Risk scoring for the primary prevention of cardiovascular disease (Review)," Cochrane Database of Systematic Reviews 2017, Issue 3. Art. No. CD006887, 155 pages, John Wiley & Sons, Ltd.

Mell et al., "The NIST Definition of Cloud Computing", National Institute of Standards and Technology, Special Publication 800-145, Sep. 2011, 7 pages.

Ford et al., "Explaining the Decrease in U.S. Deaths from Coronary Disease, 1980-2000", New England Journal of Medicine, Jun. 7, 2007, vol. 356, pp. 2388-2398.

Ibanez et al., "2017 ESC Guidelines for the management of acute myocardial infarction in patients presenting with ST-segment elevation", European Heart Journal, 2018, vol. 39, pp. 119-177, doi:10.1093/eurheartj/ehx393.

"Noncommunicable diseases and mental health, NCD Global Monitoring Framework", World Health Organization, downloaded from https://www.who.int/nmh/global_monitoring_framework/en/ on Sep. 24, 2020, 7 pages.

"Chronic diseases and health promotion, Integrated chronic disease prevention and control", World Health Organization, downloaded from https://www.who.int/chp/about/integrated_cd/en/ on Sep. 24, 2020, 20 pages.

McCarthy, "7 smartphone apps that can help improve health literacy," NueMD, Industry News, Healthcare Technology, https://www.nuemd.com/news/2017/08/03/7-smartphone-apps-can-help-improve-health-literacy, accessed Jul. 14, 2020, 8 pages.

* cited by examiner

EVALUATION OF REDUCTION OF DISEASE RISK AND TREATMENT DECISION

BACKGROUND

The present invention relates to evaluation for disease risk, and more specifically, to a method, a system, and a computer readable medium for evaluating disease risk reduction of patients.

Nowadays, chronic diseases are the leading causes of death and disability worldwide. By 2020, it is expected that chronic diseases will cause up to 73% of all deaths and 60% of the global burden of disease. Examples of major chronic diseases include diabetes, hypertension, hyperlipidemia, chronic obstructive pulmonary disease (COPD), and cardiovascular and cerebrovascular diseases. Thus, the prevention of and intervention for chronic diseases are important.

SUMMARY

According to one exemplary embodiment of the present invention, a method, a computer system, and a computer program product may evaluate a reduction of disease risk. Patient data of a patient may be received. A selection of a disease outcome may be received. A risk score that the patient will experience the selected disease outcome may be determined. The determining may use the patient data. Intervention options may be generated based on the patient data and by accessing a medical record data structure. An intervention effect for each of the intervention options may be determined. The intervention effect may change the risk score. The intervention effects may be compared. A recommendation of at least one of the intervention options may be provided based on the comparing of the intervention effects.

According to another exemplary embodiment of the present invention, a method, a computer system, and a computer program product may also evaluate a reduction of disease risk. Patient data of a patient may be received. A selection of a disease outcome may be received. A risk score that the patient will experience the selected disease outcome may be determined. The determining may use the patient data. Intervention options may be generated based on the patient data and by accessing a medical record data structure. The intervention options may include individual intervention options and at least one combination of intervention options. A reduced risk score achieved by each of the intervention options may be determined. The reduced risk scores may be compared. A recommendation of at least one of the intervention options may be provided based on the comparing of the reduced risk scores.

BRIEF DESCRIPTION OF THE DRAWINGS

Through the more detailed description of some embodiments of the present disclosure in the accompanying drawings, the above and other objects, features and advantages of the present disclosure will become more apparent. The same reference numbers generally refer to the same components in the various embodiments of the present disclosure.

DETAILED DESCRIPTION

Figure 1:
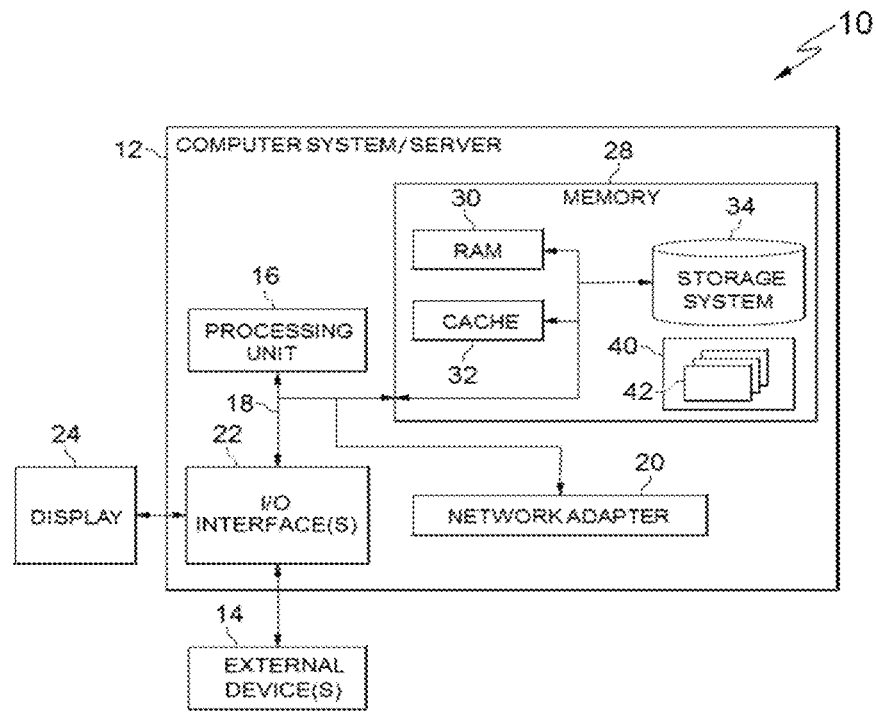
FIG. 1 depicts a cloud computing node according to an embodiment of the present invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented with and/or performing any of the functionality set forth hereinabove.

The cloud computing node 10 includes a computer system/server 12 or a portable electronic device such as a communication device, which is operational with numerous other general-purpose or special-purpose computing system environments or configurations. Examples of well-known computing systems, environments, and/or configurations that may be suitable for use with the computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system/server 12 may be described in the general context of computer system-executable instructions, such as program modules, being executed by a computer system. Generally, program modules may include routines, programs, objects, components, logic, data structures, and so on that perform particular tasks or that implement particular abstract data types. The computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, the computer system/server 12 in the cloud computing node 10 is shown in the form of a general-purpose computing device. The components of computer system/server 12 may include, but are not limited to, one or more processors or processing units 16, a system memory 28, and a bus 18 that couples various system components including the system memory 28 to the processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnect (PCI) bus.

The computer system/server 12 typically includes a variety of computer system readable media. Such media may be any available media that is accessible by the computer system/server 12, and this media includes both volatile and non-volatile media, removable and non-removable media.

The system memory 28 can include computer system readable media in the form of volatile memory, such as random access memory (RAM) 30 and/or cache memory 32. The computer system/server 12 may further include other removable/non-removable, volatile/non-volatile computer system storage media. By way of example, the storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 18 by one or more data media interfaces. As will be further depicted and described below, the system memory 28 may include at least one program product having a set (e.g., at least one) of program modules that are configured to carry out the functions of embodiments of the invention.

A program/utility 40, having a set (at least one) of program modules 42, may be stored in the system memory 28 by way of example, and not limitation. An operating system, one or more application programs, other program modules, and program data may also be stored in the system memory 28. Each of the operating systems, one or more application programs, other program modules, and program data or some combination thereof, may include an implementation of a networking environment. Program modules 42 generally carry out the functions and/or methodologies of embodiments of the invention as described herein.

The computer system/server 12 may also communicate with one or more external devices 14 such as a keyboard, a pointing device, a display 24, etc.; one or more devices that enable a user to interact with the computer system/server 12; and/or any devices (e.g., network card, modem, etc.) that enable the computer system/server 12 to communicate with one or more other computing devices. Such communication can occur via Input/Output (I/O) interfaces 22. Still yet, the computer system/server 12 can communicate with one or more networks such as a local area network (LAN), a general wide area network (WAN), and/or a public network (e.g., the Internet) via a network adapter 20. As depicted, the network adapter 20 communicates with the other components of the computer system/server 12 via the bus 18. It should be understood that other hardware and/or software components, although not shown, could be used in conjunction with the computer system/server 12. Examples, include, but are not limited to: microcode, device drivers, redundant processors, external disk drive arrays, RAID systems, tape drives, and data archival storage systems, etc.

Figure 2:
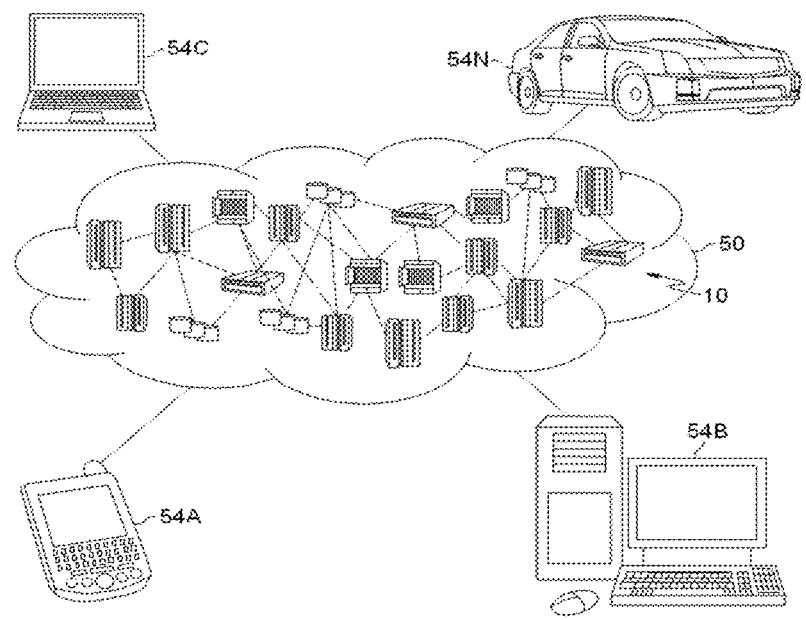
FIG. 2 depicts a cloud computing environment according to an embodiment of the present invention.

FIG. 2 depicts an illustrative cloud computing environment 50. As shown, the cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. The cloud computing nodes 10 may communicate with one another. They may be grouped (not shown) physically or virtually, in one or more networks, such as Private, Community, Public, or Hybrid clouds as described hereinabove, or a combination thereof. This allows the cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that the computing nodes 10 and the cloud computing environment 50 can communicate with any type of computerized device over any type of network and/or network addressable connection (e.g., using a web browser).

Figure 3:
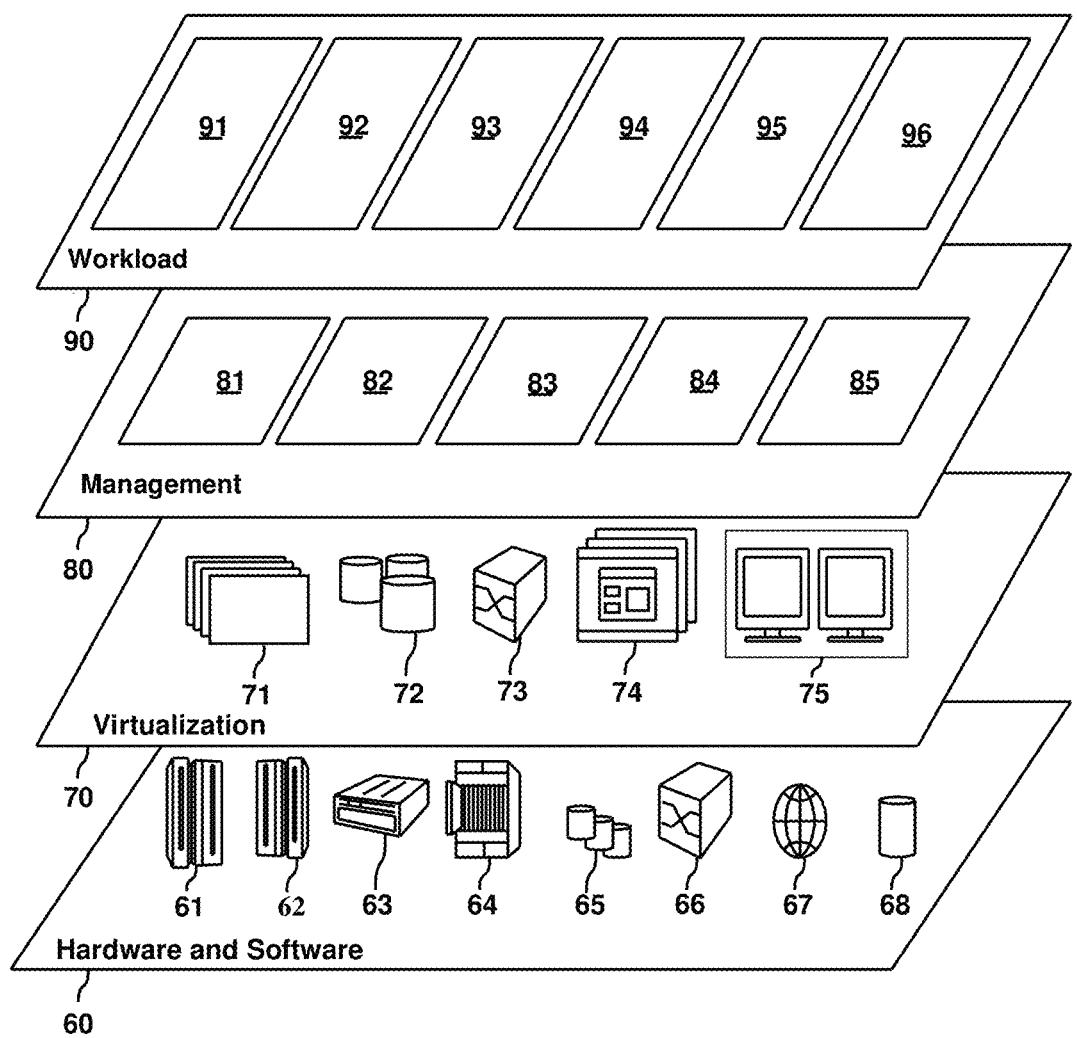
FIG. 3 depicts abstraction model layers according to an embodiment of the present invention.

Referring now to FIG. 3, a set of functional abstraction layers is shown that is provided by the cloud computing environment 50 shown in FIG. 2. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and disease risk reduction evaluation 96.

When a normal chronic disease risk assessment is performed, patient data, such as demographic data, vital signs, lab tests, etc., are received as input data. Risk assessment algorithms or models are used for a given disease outcome to obtain a risk score and to obtain corresponding medical suggestions. Here, the possible disease outcome may be having a specific disease or having an outcome caused by a disease. Death, deafness, etc. are possible outcomes. One example of the risk assessment algorithms and models is a Framingham risk model, which is used for cardiovascular diseases. In a risk assessment report for the patient, the risk score for the given disease outcome may be shown and some suggestions may be given. For example, for a patient who has a high risk to have chronic obstructive pulmonary disease (COPD), a possible suggestion for the patient may be to "quit smoking". This suggestion to affect a positive intervention to a future course of health of the patient may be referred to as an intervention suggestion.

Some intervention suggestions may be based on clinical guidelines. In such instances, an intervention suggestion may be provided to a patient based on an already-formed clinical guideline. This kind of guideline normally provides an intervention guide in generalities, however, and does not provide a quantitative assessment on what effect an intervention will achieve. Additionally, the guideline is not provided relative to a risk score.

Another method for providing an intervention suggestion includes performing a risk assessment by changing the value of a risk factor. In other words, this approach includes comparing changes in the risk score against changes in the value of the risk factor. Here, the risk factor is part of the patient data that is used as an input for a risk assessment algorithm or model. For a patient with high blood pressure, for example, the blood pressure is considered the risk factor. If the patient does not lower his or her blood pressure, i.e., does not lower the risk factor, the risk score for the patient to experience a cerebrovascular accident (CVA) could be 0.8. If the patient does lower his or her blood pressure, the risk score for the patient to have the CVA could be lowered to 0.4. The lowering of the blood pressure would constitute an intervention in the health of the patient. This method uses two assessments with different inputs to the same model but cannot show actual effectiveness of interventions. Additionally, this comparison method does not allow some risk factors such as age and sex of a patient to be controlled or changed.

Performing a quantitative assessment on intervention options for a disease has been difficult, because most researchers do not have the necessary resources or time to select and use cohorts with risk assessment scores in medically controlled experiments, so as to assess the pros and cons of different interventions for different diseases.

The method, computer system, and computer program product described herein help medical workers leverage values determined in medical research to help doctors, medical workers, and patients to quantitatively assess the effectiveness of possible health intervention measures to reduce the risks of negative health outcomes or of negative disease outcomes. With the solutions provided with this disclosure, by using published data to calculate a change in a risk score, different intervention options and different combinations of intervention options can be evaluated automatically and accurately to quantitatively provide effective recommendations without the need for researchers to perform redundant medically-controlled experiments.

Figure 4:
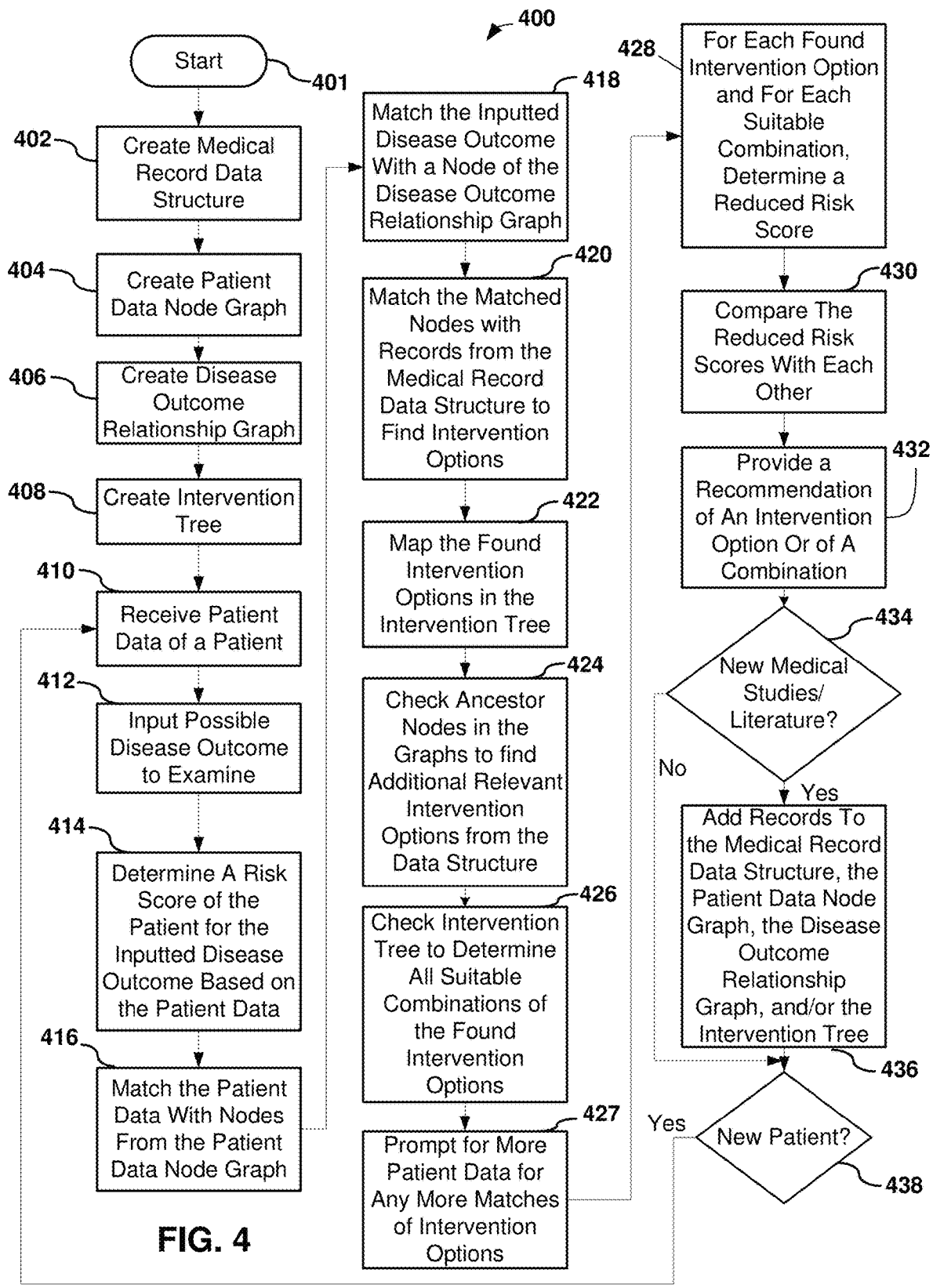
FIG. 4 is a flowchart illustrating an exemplary method to evaluate a reduction of disease risk according to an embodiment of the present disclosure.

FIG. 4 shows a flowchart that illustrates a process 400 for evaluating a reduction of a disease risk according to an embodiment of the present disclosure.

The processing of disease risk reduction evaluation according to embodiments of this disclosure may in at least some embodiments be implemented by the computer system/server 12 shown in FIG. 1.

After the start 401 of the process 400 shown in FIG. 4, step 402 is performed by creating a medical record data structure. The medical record data structure may include a knowledge table or a medical record table which provides information from medical studies which link patient data to risks and disease outcomes based on tests that were performed.

The step 402 of creating the medical record data structure may include collecting information and storing the collected information in the data structure such as a knowledge table. The data structure may include records of knowledge that may come from medical literature or medical studies. The records of knowledge of the data structure may also or alternatively include a summary of information from such pieces of medical literature or from such medical studies. Each of the records of knowledge may store information that matches specific groups of the population with patient data, with given disease outcomes, with possible intervention measures, and corresponding relative risk reductions. Table 1 that is provided below shows an example of such a knowledge table. In at least some embodiments, a record in the knowledge table may store a name or code of the referenced literature or of the referenced study.

The patient data may include, for example, demographic data, vital signs, health measurements, and/or lab test results. The demographic data may, for example, include heights, weights, ages, genders, etc. of patients who participated in the respective study. The vital signs may, for example, include body temperature, blood pressure, heart rate, respiratory frequency, etc. of those who participated in the study as patients. The lab test results may for example, include low-density lipoprotein-cholesterol (LDL-C), e.g., an LDL-C of 2 mmol/L, high-density lipoprotein-cholesterol (HDL-C), e.g., an HDL-C of 3 mmol/L, blood glucose level, e.g., a blood glucose level of 7 mmol/L, and a serum uric acid level, e.g., a serum uric acid level of 450 μmol/L, etc. The medical records may also include links between diagnostic results of patients and their patient data. For example, the patient data may include links or tendencies of patients or groups of patients to have arteriosclerotic cardiovascular disease (ASCVD), hyperlipidemia, or diabetes. These specific data mentioned above are examples. Data other than the above-provided examples can be included in the patient data that are part of the medical records included in the medical record data structure that is created. The medical records may include information about risk factors for patients and groups of patients. For example, certain vital signs, health measurements, and/or lab test results of patients may be stored in conjunction with corresponding risk factors.

Table 1 provided below is an example of a medical record data structure that may be created in step 402 of the process 400. In Table 1, the literature pieces or studies are referred to generically as R1, R2, and R3. Three rows are included, with each of the rows being an entry for information from one of the three pieces of medical literature R1, R2, and R3.

TABLE 1

| Patient Data | Intervention Measure | Outcome | RRR | Literature |
| --- | --- | --- | --- | --- |
| P1 | I1 | O1 | 0.31 | R1 |
| P1 | I2 | O1 | 0.23 | R2 |
| P3 | I2 | O2 | 0.15 | R3 |

In Table 1, information from the literature R1 is included indicating that for a patient with patient data P1, if the intervention measure I1 is used the risk for the disease outcome O1 could be reduced by 0.31. Table 1 is one example of a medical record data structure that may be created in step 402.

In another embodiment of the disclosure, a knowledge table may lack the column of "Patient Data", and the recorded RRR for an intervention measure would apply to all possible patients or to everybody. In a further embodiment of the disclosure, the collected information may be organized into a plurality of tables. These tables may, for example, lack the "Outcome" column and each of the tables may be used for a specific outcome.

The ways of organizing the collected information as shown in the examples are not the only possible ways according to the disclosure. Other ways of information organization are also possible according to the disclosure.

Figure 9A:
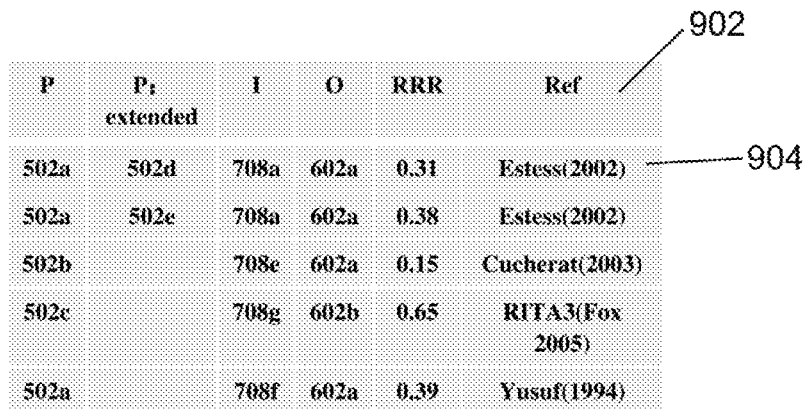
FIG. 9A shows an example of a medical record data structure according to one embodiment of the disclosure.

The medical record table 902 shown in FIG. 9A is an example of a medical record data structure according to some embodiments. The medical record table 902 will be used as part of EXAMPLE A of performing process 400 that will be further described in the subsequent disclosure. The medical record table 902 includes six columns and five rows. Each column represents a different category of information. Each row corresponds to information from a different medical study or different piece of medical literature. Thus, the medical record table 902 includes a first medical record table row 904 and additionally includes four other data rows corresponding to and holding information from four other medical studies or from four other pieces of medical literature as well. The first medical record table row 904 provides information regarding a medical study that was authored by Estess and was published in 2002.

Figure 5:
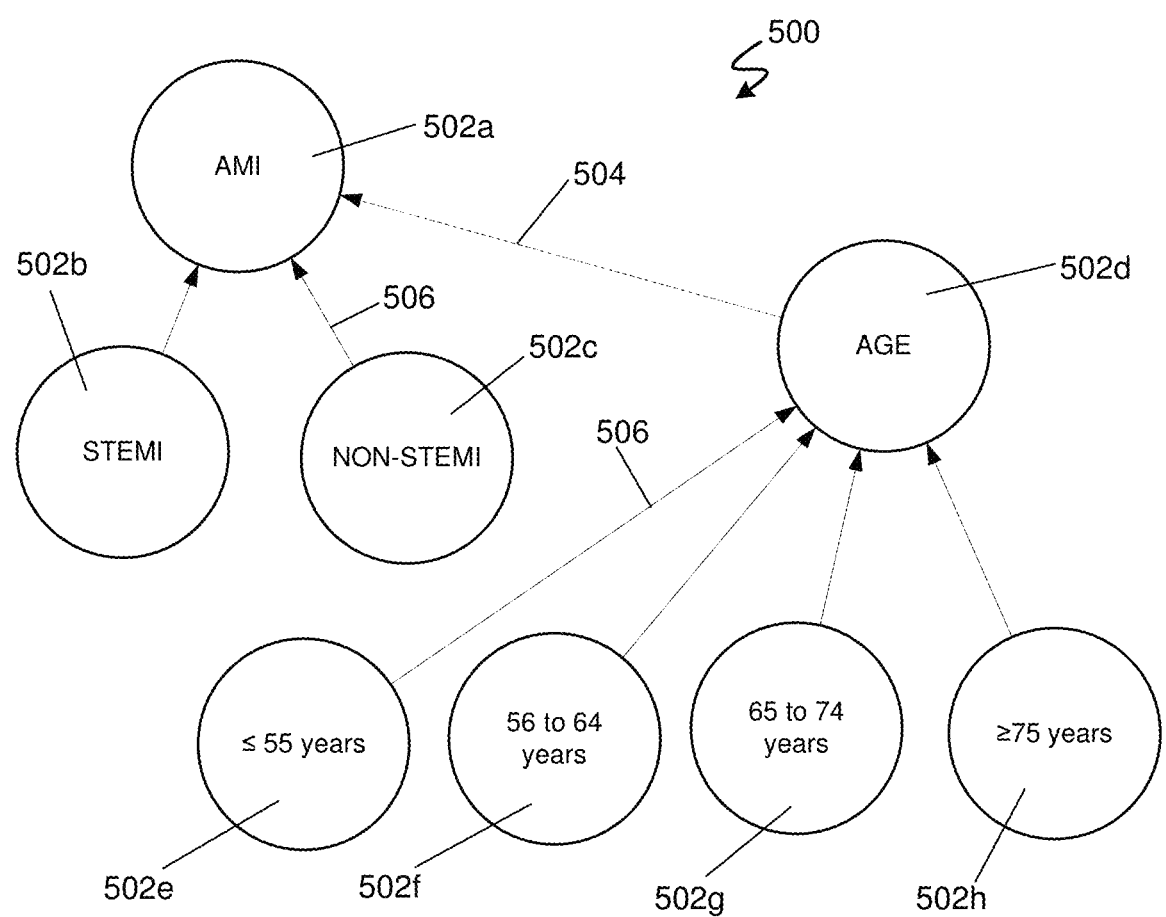
FIG. 5 shows an example of a patient data node graph according to one embodiment of the disclosure.
Figure 6:
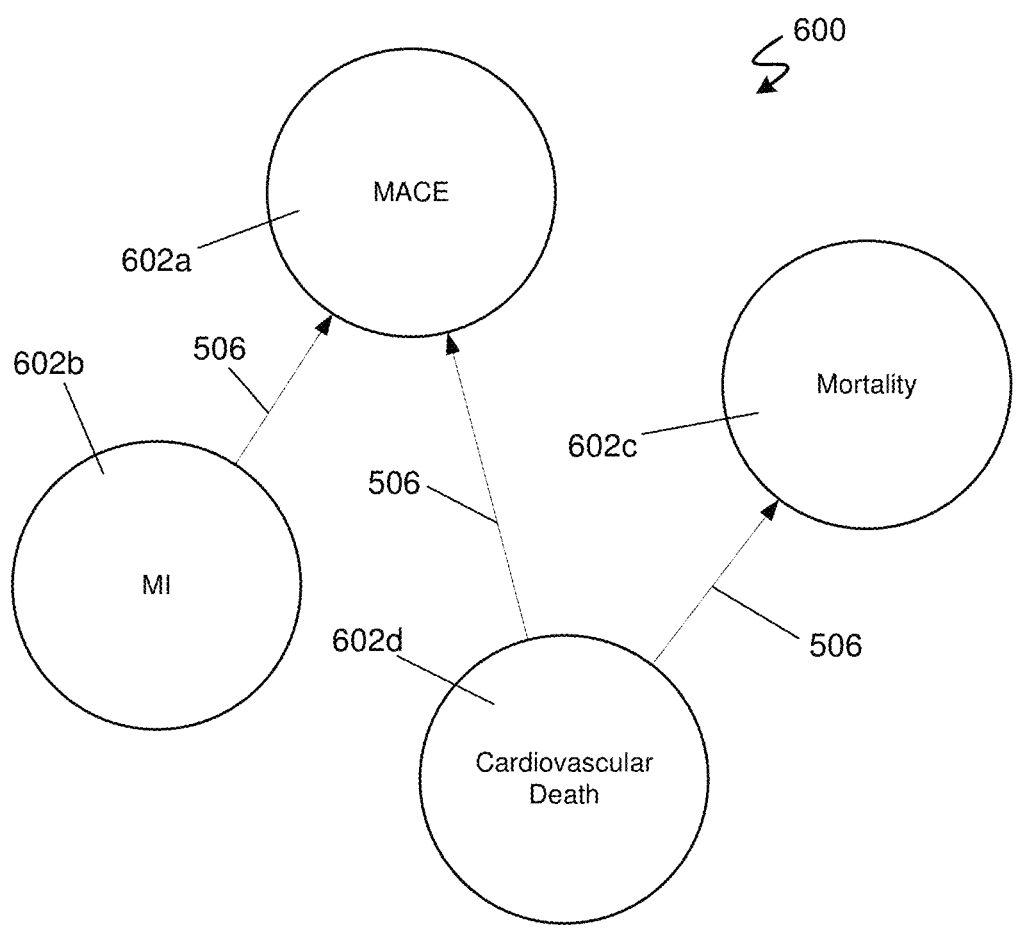
FIG. 6 shows an example of a disease outcome relationship graph according to one embodiment of the disclosure.
Figure 7:
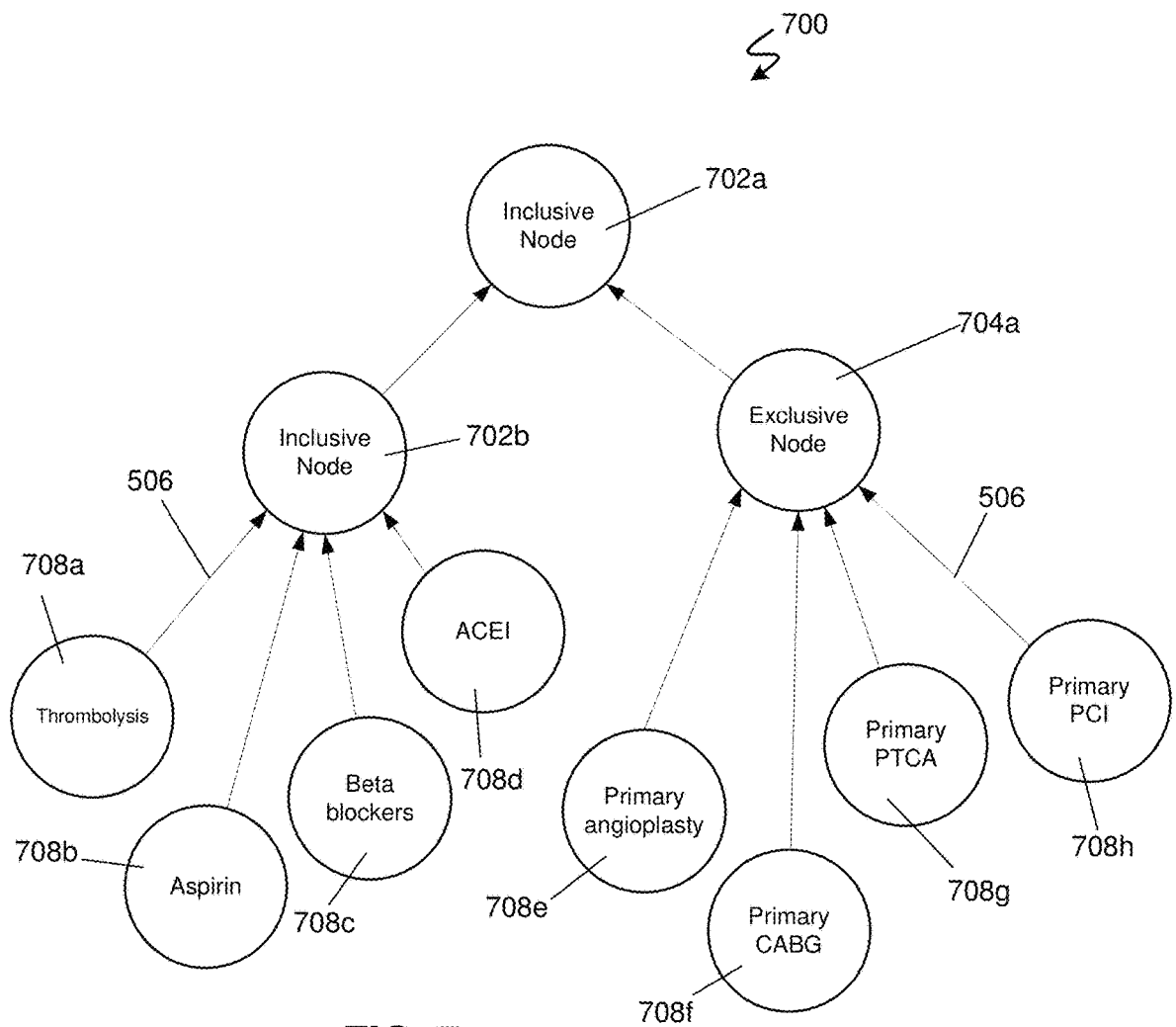
FIG. 7 shows an example of an intervention tree that illustrates relationships among intervention measures according to one embodiment of the disclosure.

The first and second columns "P" and "P: extended" provide patient data information. The references in the first and second columns refer to entries in or nodes of a patient data node graph 500 that will be described subsequently and that is shown in FIG. 5. The third column "I" refers to entries or nodes from an intervention tree 700 that will be described subsequently and that is shown in FIG. 7. The fourth column "O" refers to entries in or nodes of a disease outcome relationship graph 600 that will be described subsequently and that is shown in FIG. 6. The fifth column "RRR" refers to a relative risk reduction value which will be described subsequently in more detail. The relative risk reduction in the fifth column is a value indicating a reduction or a relative risk reduction with respect to the chances that patients who meet the patient data categories in the first two columns and who were subjected to the intervention option indicated in the third column will incur the disease outcome indicated in the fourth column. This relative risk reduction amount in the fifth column may be indicated in the medical study or piece of medical literature to which the row pertains, e.g., the RRR of 0.31 which reduces risk of incurring the disease outcome for 602a was indicated in the Estess 2002 medical study regarding patients who have patient data of 502a and 502d and who were subjected to the intervention option of 602a.

Thus, the medical record table 902 when used in conjunction with additional graphs or trees may provide more information than is provided in the Table 1, and specifically may provide more information in the columns for Patient Data, Intervention Measures, and Outcomes, including hierarchical information about relationships of patient data, outcomes, and intervention measures.

The medical record data structure may be created manually by a medical worker who collects and reviews various medical studies and/or various pieces of medical literature. Alternatively, the medical record data structure may be created by a computer program that performs natural language processing (NLP) techniques and that scans medical studies and/or pieces of medical literature that are uploaded into the computer, e.g into the computer system/server 12. Additionally or alternatively, the computer program may generate a scanning of the internet for published medical studies and/or published pieces of medical literature and may generate a collecting of such published works or pieces and a performing of natural language processing (NLP) techniques to look for new suitable studies or medical literature which have data suitable to be entered into the medical record data structure. The medical record data structure may be created in spreadsheet software or in some other suitable information storage software that allows the stored information to be quickly and efficiently searched and analyzed by a processor, e.g. by the processing unit 16. The medical record data structure may be stored in a memory, e.g., in the memory 28, and may be displayed on a screen, e.g., on display 24.

In step 404 of the process 400 a patient data node graph is created. FIG. 5 shows an example of a patient data node graph 500 according to one embodiment of the disclosure. The patient data node graph 500 is part of the EXAMPLE A that was introduced above for step 402. The patient data node graph 500 illustrates relationships among two different types of patient data—one from a diagnostic result, namely a diagnostic result of Acute Myocardial Infarction (AMI), and the other from the age of the patient.

When a patient receives a diagnostic result of Acute Myocardial Infarction (AMI), this diagnostic result of AMI can be classified into two sub-types: ST-Segment-Elevation Myocardial Infarction (STEMI) and Non-ST-Segment-Elevation Myocardial Infarction (NON-STEMI). Considering that some literature may involve treatment for only one sub-type of AMI, e.g., may involve treatment for STEMI but not for NON-STEMI, this classification to the two sub-types can help provide a more accurate prediction. The patient data node graph 500 in FIG. 5 shows the relationships among AMI, STEMI, and NON-STEMI diagnoses. The medical record table 902 shown in FIG. 9A has entries in its first and second columns that refer to nodes from the patient data node graph 500.

The patient data node graph 500 in FIG. 5 may also be considered a data structure and shows how hierarchical information between patient data may be indicated and stored. In FIG. 5, the diagnostic results of AMI, STEMI and NON-STEMI are shown as first, second, and third patient data nodes 502a, 502b, and 502c in a graph. Here, the solid arrows 506 in FIG. 5 represent a relationship between the entities represented by the nodes. For the relationship, an entity or information represented by the starting node of the solid arrows 506 is a sub-type of the entity or information represented by the ending node of the arrow. For example, in FIG. 5, a STEMI diagnosis (indicated by second patient data node 502b) is a sub-type of an AMI diagnosis (indicated by first patient data node 502a). A NON-STEMI diagnosis (indicated by third patient data node 502c) is also a sub-type of an AMI diagnosis (indicated by first patient data node 502a).

In some embodiments, the patient data can also include extended data such as age. Thus, with this embodiment a combination of age and diagnostic results can be used for matching in the medical record data structure. In FIG. 5, the fourth patient data node 502d represents patient data regarding the age of the patients. The dashed arrow 504 starting from the fourth patient data node 502d ends at the first patient data node 502a. The dashed arrow 504 represents that "age" is associated with the "AMI" diagnosis for evaluation purposes and for predictive purposes.

In FIG. 5, the patient data node graph 500 classifies the ages of the patients into four groups: ≤55 years old (represented by the fifth patient data node 502e), 56-64 years old (represented by the sixth patient data node 502f), 65-74 years old (represented by the seventh patient data node 502g), and ≥75 years old (represented by the eighth patient data node 502h). A solid arrow 506 runs from each of the fifth, sixth, seventh, and eighth patient data nodes 502e, 502f, 502g, 502h to the fourth patient data node 502d and indicates that each of the fifth, sixth, seventh, and eighth patient data nodes 502e, 502f, 502g, 502h represents information that is a sub-type of the information represented by the fourth patient data node 502d.

The patient data node graph 500 may be created manually by a medical worker who collects and reviews various medical studies and/or various pieces of medical literature and/or a medical record data structure that is created in step 402. Alternatively, the patient data node graph 500 may be created by a computer program that performs natural language processing (NLP) techniques and that scans medical studies and/or pieces of medical literature and/or data structures that are uploaded into the computer, e.g., into the computer system/server 12. Additionally or alternatively, the computer program may generate a scanning of the internet for published medical studies and/or published pieces of medical literature and may generate a collecting of such published works or pieces and a performing of natural language processing (NLP) techniques to look for new suitable studies or medical literature which have data suitable to be entered into the patient data node graph 500. The patient data node graph 500 may be created using a graphing software or using some other suitable software that allows information to be stored in a graph form and then quickly and efficiently searched and analyzed by a processor. The patient data node graph 500 may be stored in a memory, e.g., in the memory 28, and may be displayed on a screen, e.g., on display 24.

The patient data node graph 500 may be used in conjunction with a medical record data structure to help guide medical care workers and patients to better determine what medical and patient effects have been produced or achieved with certain medical interventions and, therefore, what possible interventions are best to recommend.

In step 406 of the process 400 a disease outcome relationship graph is created. FIG. 6 shows an example of a disease outcome relationship graph 600 according to one embodiment of the disclosure. The disease outcome relationship graph 600 in FIG. 6 is part of the EXAMPLE A that was introduced above in the description regarding steps 402 and 404. The disease outcome relationship graph 600 illustrates relationships among certain possible disease outcomes that can result from certain diseases. The disease outcome relationship graph 600 in FIG. 6 may also be considered a data structure and shows one way how hierarchical information regarding disease outcomes may be indicated and stored.

In FIG. 6, the solid arrows 506 have the same meaning as the solid arrows 506 that are used in FIG. 5. For example, one of the solid arrows 506 indicates that the second disease outcome node 602b represents an outcome that is a sub-type of the outcome represented by the first disease outcome node 602a. According to FIG. 6, Myocardial infarction (MI) (represented by the second disease outcome node 602b) is a sub-type of Major Adverse Cardiovascular Events (MACE) (represented by the first disease outcome node 602a). Cardiovascular death (represented by the fourth disease outcome node 602d) is a sub-type of MACE (represented by the first disease outcome node 602a) and is also a sub-type of Mortality (represented by the third disease outcome node 602c).

The disease outcome relationship graph 600 may be created manually by a medical worker who collects and reviews various medical studies and/or various pieces of medical literature and/or a medical record data structure that is created in step 402. Alternatively, the disease outcome relationship graph 600 may be created by a computer program that performs natural language processing (NLP) techniques and that scans medical studies and/or pieces of medical literature and/or data structures that are uploaded into the computer, e.g., into the computer system/server 12. This computer program may additionally or alternatively also generate a scanning of the internet for published medical studies and/or published pieces of medical literature and may generate a collecting of such published works or pieces and may perform natural language processing (NLP) techniques to look for new suitable studies or medical literature which have data suitable to be entered into the disease outcome relationship graph 600. The disease outcome relationship graph 600 may be created using graphing software or using some other suitable software that enables information to be stored in a graph form and then quickly and efficiently searched and analyzed by a processor. The disease outcome relationship graph 600 may be stored in a memory, e.g., in the memory 28, and may be displayed on a screen, e.g., on display 24.

The disease outcome relationship graph 600 may be used in conjunction with a medical record data structure and optionally with a patient data node graph 500 to help guide medical care workers and patients to better determine what medical and patient effects have been produced with certain medical interventions and, therefore, what interventions are best to recommend to reduce risks of incurring possible negative disease outcomes.

In step 408 of the process 400 an intervention tree is created. FIG. 7 shows an example of an intervention tree 700 according to one embodiment of the disclosure. The intervention tree 700 in FIG. 7 is part of the EXAMPLE A that was introduced above regarding steps 402, 404, 406. The intervention tree 700 illustrates relationships among certain possible disease intervention options that can be performed to intervene and reduce the chances that patients experience negative outcomes. The intervention tree 700 in FIG. 7 may also be considered a data structure and shows how hierarchical information regarding various intervention options may be indicated and stored. Some interventions when applied to the patient may not be performed or applied in combination with other interventions. Such interventions may be referred to as exclusive interventions. Alternatively, some interventions may be performed in combination with one or more other intervention measures and may be referred to as inclusive measures. An intervention may include one or more pharmaceutical measures and/or one or more non-pharmaceutical measures. For example, an intervention may include both the intervention of "quit smoking" which may be considered a non-pharmaceutical measure and an intervention "taking Aspirin" which is a pharmaceutical measure.

FIG. 7 shows the intervention tree 700, whose leaf nodes represent intervention measures. The first and second inclusive nodes 702a and 702b in FIG. 7 indicate that it is advisable or possible for intervention measures of at least some of their child nodes to be applied to a patient in a combined manner. For example, it may be suitable for a patient to receive a Thrombolysis (represented by the first intervention node 708a) in combination with the regular taking of Aspirin (represented by the second intervention node 708b). Thrombolysis, also known as thrombolytic therapy, includes the use of medicine to dissolve dangerous clots in blood vessels, to improve blood flow, and to prevent damage to tissues and organs. Thrombolysis (represented by the first intervention node 708a) can also be applied in a combined manner with beta blocker treatments (represented by the third intervention node 708c) and/or with Angiotensin-converting-enzyme inhibitors (ACEI) (represented by the fourth intervention node 708d). Beta blockers, also known as beta-adrenergic blocking agents, are medications or pharmaceuticals that reduce blood pressure. In some instances, the first, second, third, and fourth intervention nodes 708a, 708b, 708c, 708d, which may be considered inclusive interventions, may also be applied to a patient in a combined manner with an exclusive intervention such as those described below corresponding to the fifth, sixth, seventh, and eighth intervention nodes 708e, 708f, 708g, 708h.

The first exclusive node 704a in FIG. 7 denotes that its child nodes must usually be adopted exclusively when used as an intervention to a patient. For example, the interventions of Primary angioplasty (represented by the fifth intervention node 708e), primary coronary artery bypass surgery ("CABG") (represented by the sixth intervention node 708f), primary percutaneous transluminal coronary angioplasty ("PTCA") (represented by the seventh intervention node 708g), and primary percutaneous coronary intervention ("Primary PCI") (represented by the eighth intervention node 708h) cannot be adopted in a combined manner with any of each other, but rather must be performed independently of the other exclusive intervention nodes which share the same parent node, in this case which share the first exclusive node 704a as a parent node or an ancestor node. In the case of exclusive node 704a and its four child nodes, the interventions represented by these fifth, sixth, seventh, and eighth intervention nodes 708e, 708f, 708g, 708h must be performed to a patient independently and not in conjunction with each other. In some embodiments, the interventions which branch from an exclusive node may not be combined with any other intervention including with any intervention that is a child node of or branches from an inclusive node such as the second inclusive node 702b, e.g. in some embodiments may not be combined with any of the first, second, third, and fourth intervention nodes 708a, 708b, 708c, 708d.

The first inclusive node 702a is shown as having some grand-children nodes that represent inclusive interventions. These nodes representing inclusive interventions are the first, second, third, and fourth intervention nodes 708a, 708b, 708c, 708d. The first inclusive node 702a is shown as also having some grand-children nodes that represent exclusive interventions. These nodes representing exclusive interventions are the fifth, sixth, seventh, and eighth intervention nodes 708e, 708f, 708g, 708h. The second inclusive node 702b is shown in FIG. 7 as having children nodes that exclusively represent inclusive interventions. Thus, an inclusive node may have all or some descendant nodes representing nodes that represent inclusive interventions. An exclusive node will usually have all descendant nodes as representing interventions that need to be applied to a patient not in combination with each other (not in combination with any of these other particular descendant nodes).

The representations of patient data, disease outcome relationships, and interventions by graphs or trees are not mandatory in some embodiments. Nevertheless, this kind of structuring of data enables more precise organization of information that is collected from literature or from studies. Thus, this kind of structuring can help achieve more accurate matching and prediction.

Step 410 of the process 400 shown in FIG. 4 is to receive patient data of a patient. The patient is a person or animal for whom a reduction in their disease risk may be evaluated. In one embodiment, the patient data may include one or more patient data items or elements. These data items or elements may include demographic data, vital signs, health measurements, and/or lab test results of the patient. The demographic data may include the name, the height, the weight, the age, the sex, etc. of a patient. The vital signs may include body temperature, blood pressure, heart rate, respiratory frequency, etc. of a patient. The lab test results may include low-density lipoprotein-cholesterol (LDL-C), e.g., an LDL-C of 2 mmol/L, high-density lipoprotein-cholesterol (HDL-C), e.g., an HDL-C of 3 mmol/L, blood glucose level, e.g., a blood glucose level of 7 mmol/L, and a serum uric acid level, e.g., a serum uric acid level of 450 µmol/L, etc. In another embodiment, the patient data may also include diagnostic results for the patient. For example, the patient data may indicate that the patient has been diagnosed as having arteriosclerotic cardiovascular disease (ASCVD), hyperlipidemia, or diabetes. These data are examples, and data other than the above-provided examples can be included in the patient data. The patient data may include a risk factor for the patient. For example, certain vital signs, health measurements, and/or lab test results of the patient may be considered risk factors. In other words, in at least some embodiments risk factors used by a model may be a subset of the patient data.

For the EXAMPLE A that was introduced above with respect to steps 402, 404, 406, and 408, the patient data that is received includes data indicating that the patient is 60 years old and has been diagnosed as having a STEMI.

This patient data may be received by a computer, e.g., the computer system/server 12, after an individual, doctor, or other medical worker accesses the computer in which the medical record data structure and optionally the patient data node graph 500, the disease outcome relationship graph 600, and the intervention tree 700 are stored. The medical record data structure, the patient data node graph 500, the disease outcome relationship graph 600, and the intervention tree 700 may be stored in a memory of that computer, e.g., in the memory 28. That computer may be located at a medical facility or may be stored remotely in a computer that is accessible through the cloud and, therefore, may be accessed by a patient or by a medical worker or a doctor. The patient may access a web site or app which uses a graphical user interface to ask the patient for personal physical information. The website or app may then pass the personal physical information to the computer as patient data.

Alternatively, a medical worker or doctor may access the website or app and provide the patient physical information as patient data via the graphical user interface. The medical worker or doctor may manually obtain data from a patient about their physical information. The medical worker or doctor may provide a physical questionnaire which the patient fills out and returns. The medical worker or doctor may alternatively have a computer in their foyer or office which a patient can access to provide patient data that may be received by another computer in which a disease risk reduction evaluation program is stored. The medical worker or doctor may alternatively visually see information about the patient and then type in information into the website, app, or computer program. The medical worker or doctor may thereby use a graphical user interface of a website or app to enter the personal physical information into the computer or computing node. Then, in instances where the medical record data structure is stored at another computer, the website or app may pass the personal physical information as patient data to the computer that hosts the medical record data structure. In instances where the medical record data structure is stored on a local computer of a medical worker or of a doctor, e.g., at their medical office, the medical worker or doctor may type in the personal physical information using a keyboard or a touch screen, e.g., the external device 14, or may speak into a microphone so that the local computer may process and use that information with respect to the medical record data structure and perhaps with respect to the graphs and the tree.

In step 412 of the process shown in FIG. 4, a possible disease outcome whose possibility is to be examined is input into the computer system or is received by the computer system. The medical worker or the patient may be concerned about the possibility of the patient experiencing or undergoing a certain disease outcome, and the overall method will at least partly be based on evaluating how the risk of the patient experiencing that disease outcome may be reduced and may most effectively be reduced. Thus, the system will need to know what disease outcome is desired to be analyzed and whose risk is desired to be reduced. The patient or medical worker may input the possible disease outcome into a graphical user interface that is generated by the computer program and displayed on a screen, e.g., on the display 24. The computer program may alternatively generate a list of various possible disease outcomes that is displayed on display 24 and may give the patient or medical worker the option to scroll through the generated list using the external device 14 to select one of the disease outcomes.

For example, a medical worker or a patient may input in the step 412 that they are interested in determining to explore the risks of a possible disease outcome of Major Adverse Cardiovascular Events (MACE) based on their patient data. This disease outcome of MACE will be used for an example disease outcome that is input in the example of this process 400 according to EXAMPLE A that has been described above for previous steps. Thus, the evaluation for disease risk reduction performed in the EXAMPLE A will evaluate what intervention will best help reduce the risk that the 60-year-old patient who experienced a STEMI will experience another MACE, e.g. within a particular time frame.

In step 414 of the process shown in FIG. 4, a risk score that the patient will experience the selected disease outcome that was input is determined. The determining uses the patient data that was received in step 410. The determining of the risk score may include computing the risk score by using a risk assessment algorithm or model. The risk score is directed to a specific disease outcome. One example of a risk assessment algorithm or model that may be used is the Framingham risk model, which is used for cardiovascular diseases. In one embodiment of the present disclosure, the risk score r is denoted as r=f(x). X is a vector having elements that are composed of the patient data, including risk factors of the patient that are needed by the risk assessment algorithm or model. r is the risk score that the patient will have, experience, or incur the given disease outcome. f( ) here represents a function relationship between r and X f(X) is the risk model for calculating the risk score against individual patient data. The risk model can be acquired by applying data analysis via machine learning, deep learning, or other technologies on patient history data according to medical research methodology.

For EXAMPLE A indicated above, for step 414 some entry in a medical record data structure and that corresponds to medical literature or originated from a medical study indicates that for patients who are between the ages of 57 and 63 years old and who have been diagnosed as having a STEMI the risk score of another MACE is 0.43.

EXAMPLE B is introduced below and illustrates determining risk scores by performing calculations according to some embodiments. In EXAMPLE B, a risk model of calculating a MACE risk (Major Adverse Cardiac Events) of a patient who has had an AMI (acute myocardial infarction) includes three risk factors: age, white blood count (WBC), and Killip Level (killip score). The risk model calculates the risk of whether the patient will have a MACE event within thirty days of the AMI. White blood count is a lab test result. Killip Level is a diagnosis of the patient by a doctor after the doctor has examined the patient following the AMI. An AMI (acute myocardial infarction) is a type of MACE (Major Adverse Cardiac Events), so the risk score indicates a likelihood of whether these patients will experience a second MACE, e.g., a second myocardial infarction, e.g., within a short-term time period such as thirty days. The risk model for this EXAMPLE B to produce the risk score f(X) for mortality is a LR (Logistic Regression) model indicated in equation (1) provided below:

$$f(x) = \frac{1}{1 + e^{8.230 - 0.056 * age - 0.095 * wbc - killip\_score}} \quad (1)$$

where $$killip\_score = \begin{cases} 0, & Killip\_level = 1 \\ 0.295, & Killip\_level = 2 \\ 1.007, & Killip\_level = 3 \\ 2.647, & Killip\_level = 4 \end{cases}$$

The Killip classification is a system used in individuals who have experienced an AMI and accounts for a physical examination and the development of heart failure in order to predict and stratify their risk of mortality. Individuals with a low Killip class are less likely to die within the first 30 days after their myocardial infarction than individuals with a high Killip class. The four Killip classes are defined as follows:

Killip class I includes individuals with no clinical signs of heart failure.

Killip class II includes individuals with rales or crackles in the lungs, an $S_3$, and elevated jugular venous pressure.

Killip class III describes individuals with frank acute pulmonary edema.

Killip class IV describes individuals in cardiogenic shock or hypotension (measured as systolic blood pressure lower than 90 mmHg), and evidence of peripheral vasoconstriction (oliguria, cyanosis or sweating).

Calculations for five different patients who had been diagnosed with AMI were performed as part of EXAMPLE B using the above-mentioned risk model to determine their risk of experiencing or undergoing mortality, i.e. death. Patient data from the five patients were placed into the first three columns of Table 2 below, and the risk score that was calculated for each patient based on the formula and the three variables is provided in the fourth column.

TABLE 2 for EXAMPLE B

| X | | | |
|---|---|---|---|
| Age | WBC (10^9/L) | Killip_level | f(X) = risk score |
| 89 | 12 | 3 | 0.249 |
| 56 | 22 | 4 | 0.412 |
| 45 | 23 | 2 | 0.038 |
| 45 | 21 | 3 | 0.062 |
| 34 | 11 | 2 | 0.007 |

The calculations indicate that the second patient (the 56-year-old patient) has the highest risk of another MACE within thirty days, while the fifth patient (the 34-year-old patient) has the lowest risk of another MACE within thirty days.

One patient data item or element from patient data that is received may be a risk factor for a first risk assessment model, but may not be a risk factor for a second risk assessment model. For example, for a model for assessing risk of pneumonia, the patient data item of whether the patient smokes may be a risk factor. For a model for assessing risk of arthritis, however, the patient data item of whether a patient smokes may be not a risk factor.

An absolute risk (AR) is defined as a ratio of the number of people experiencing an event to the number of people in the population. If two groups of people or patients include a first group that is subjected to an intervention measure and a second group that is not subjected to the intervention measure, the first group is called a treatment group and the second group is called a control group or a reference group. In the control group, the AR of a specific event, e.g., of experiencing a particular disease outcome, is denoted as absolute risk of the control group (ARC). In the treatment group, the AR of the specific event, e.g., of experiencing a particular disease outcome, is denoted as absolute risk of the treatment group (ART).

In some alternative embodiments, the risk score determined in step 414 may be determined by looking up the data from the medical record data structure that was created in step 402. With these embodiments, medical studies or pieces of literature whose information is already stored in the medical record data structure may have already determined risk scores for different groups of patients with respect to certain potential disease outcomes. The risk score or those risk scores may be entered into the medical record data structure in step 402, so that the determining of the risk score in step 414 may include accessing the medical record data structure and pulling the risk score from the medical record data structure based on the patient data. The computer program may generate a search through entries saved in the medical record data structure using patient data as input to find matches in entries that also have the same patient data. Then the risk score associated with that entry may be returned to the processor or to the medical worker or may be temporarily saved for calculations to be performed by the computer program.

For example, in a medical record data structure that is similar to the medical record table 902 that is shown in FIG. 9A, a column may be present entitled "r" for risk score. This alternative medical record data structure may indicate that for patients who are between 50 and 59 years old and have received lab test results indicating that their total cholesterol level is 290 mg/dL, the r for MACE (represented by the first disease outcome node 602a from FIG. 6) may be 0.6, the r for MI (represented by the second disease outcome node 602b from FIG. 6) may be 0.35, the r for mortality (represented by the third disease outcome node 602c from FIG. 6) may be 0.5, and the r for cardiovascular death (represented by the fourth disease outcome node 602d from FIG. 6) may be 0.2.

In step 416 of the process 400 shown in FIG. 4, the patient data received in step 410 is matched with one or more nodes from the patient data node graph 500 that is shown in FIG. 5. This step may be performed by text-searching software which scans or reads through the information and text stored in the patient data node graph 500 to compare the text and information there to the text and information of the patient data. Software with logic comparison features may also be used, for example when a patient data is a specific age but the nodes represent a range of possible ages of the patient. This software may be used and programmed to perform the required matching.

For example, following EXAMPLE A wherein the patient data received in step 410 includes age information that the patient is 60 years old and that the patient received a diagnosis of a STEMI, the processor may take this patient data and as part of step 416 scan the patient data node graph 500 to match the age data and the STEMI diagnosis with the sixth patient data node 502f and with the second patient data node 502b, respectively. This matching node information may be useful to the computer system in subsequent steps when it searches through a medical record data structure which is coded with the node numbers that are provided in the patient data node graph 500. This matching node information may be stored in a memory, e.g., in memory 28, that is connected to the processor, e.g. the processing unit 16, to be available to access for subsequent matching and mapping.

In step 418 of the process 400 shown in FIG. 4, the disease outcome that was input in step 412 is matched with a node from the disease outcome relationship graph 600 that is shown in FIG. 6. The same software or similar software described above that was used to perform the matching of step 416 may also be used and programmed to perform the matching of step 418.

For the EXAMPLE A in which the possible disease outcome of Major Adverse Cardiovascular Events (MACE) was selected and input as explained above in step 412, the matching in step 418 would include scanning the disease outcome relationship graph 600 to match the inputted disease with the first disease outcome node 602a which represents the disease outcome of MACE. This matching node information may be useful to the computer system in subsequent steps when it searches through a medical record data structure which is coded with the node numbers that are provided in the disease outcome relationship graph 600. This matching node information may be stored in a memory, e.g., in memory 28, that is connected to the processor, e.g., the processing unit 16, to be available to access for subsequent matching and mapping.

In step 420 of the process 400 shown in FIG. 4, the matched nodes from steps 416 and 418 are matched with records from the medical record data structure that was created in step 402. This matching of step 420 is used to find intervention options relevant to the patient data that is received and to the disease outcome that is desired to be analyzed and whose risk is desired to be reduced. The same software or similar software described above that was used to perform the matching of steps 416 and 418 may also be used and programmed to perform the matching of step 420. The relevant intervention options found may be stored in a memory, e.g., memory 28, connected to the processor, e.g., the processing unit 16, to be available to access for subsequent matching and mapping.

In EXAMPLE A, when the sixth patient data node 502f and the second patient data node 502b that were matched in step 416 and the first disease outcome node 602a that was matched in step 418 are used for step 420, they may be matched with records from the medical record table 902 that is shown in FIG. 9A. The medical record table 902 is an example of a medical record data structure.

The matching of step 420 for EXAMPLE A may recognize that the first medical record table row 904 as well as the second, third, and fifth data rows are matches of the first disease outcome node 602a, but that the fourth data row is not a match. The fourth data row is not a match because its entry "602b" in the disease outcome column O corresponds to the second disease outcome node 602b and not to the first disease outcome node 602a.

The matching of step 420 in EXAMPLE A may also recognize in the matching for the patient data nodes that the third data row alone is an initial match for the second patient data node 502*b* and for the sixth patient data node 502*f*. The third data row is the only data row with an entry of "502*b*" corresponding to the second patient data node 502*b*. Although the third data row does not include any express match for the sixth patient data node 502*f*, the third data row does not include any node information that conflicts with the sixth patient data node 502*f*. The third data row has a blank entry for the "P: extended" column and, therefore, has no patient data that conflicts with the sixth patient data node 502*f*.

A comparison of the matching of the patient data nodes in the medical record table 902 (first, second, third, and fifth data rows is a patient match) and the matching of the disease outcome nodes in the medical record table 902 (third data row is an outcome match) that were performed in step 420 of EXAMPLE A indicates that for initial matching the third data row alone is a matching row that should be used to find an intervention option. Thus, the intervention information "708*e*" indicated in the third column "I" in the third data row is considered to have been found by the initial matching.

Thus, when multiple nodes, such as multiple patient data nodes, are used for matching, a row or data segment in the medical record data structure may be considered if a match if at least one patient data node matches with the row or data segment and if no entry in the row or segment conflicts with any other patient data node. Of course, if each of multiple patient data nodes matches with an entry or segment in the data structure, then that group of multiple patient data nodes would also be considered to match with the row or data segment.

In step 422 of the process 400 shown in FIG. 4, the intervention options that were found in step 420 are mapped in the intervention tree that was created in step 408. The same software or similar software described above that was used to perform the matching of steps 416, 418, and 420 may also be used and programmed to perform the mapping of step 422. The mapping will show or reveal the specific intervention option based on the intervention option information found in step 420. This specific intervention option may then be stored in a memory, e.g., memory 28, connected to the processor, e.g., processing unit 16, to be available to access for subsequent presentation to the medical worker or patient when a recommendation is provided.

Building on EXAMPLE A provided above in which the nodes matched into the medical record table 902 resulted in the intervention entry "708*e*" being found, the mapping of this intervention entry "708*e*" into the intervention tree 700 in EXAMPLE A indicates that this entry corresponds to the fifth intervention node 708*e* which represents the intervention option of a primary angioplasty. The mapping of step 422 for EXAMPLE A may also indicate that the fifth intervention node 708*e* is a child node of a first exclusive node 704*a*, which indicates that the primary angioplasty represented by the fifth intervention node 708*e* may not be performed in conjunction with several other possible interventions represented by the other child nodes of the first exclusive node 704*a*, namely may not be performed in conjunction with the treatments or intervention options that correspond to the sixth, seventh, and eighth intervention nodes 708*f*, 708*g*, 708*h*. This possible intervention that the patient could receive a primary angioplasty may for EXAMPLE A be stored in the memory, e.g., memory 28, to be ready to be presented to the patient later as part of a recommendation.

In step 424 of the process 400 shown in FIG. 4, ancestor nodes in the graphs, the medical record data structure, and/or the intervention tree are checked to find additional relevant intervention options. The ancestor nodes would be ancestors of the nodes that were matched in steps 416, 418, and 422. An ancestor node of a first node may be a node connected to the first node that is higher in the hierarchy defined by a node graph. The same software or similar software described above that was used to perform the matching of steps 416, 418, and 420 and the mapping in step 422 may also be used and programmed to perform the checking of step 424. The additional relevant intervention options that are found may then be stored in a memory, e.g., memory 28, connected to the processor, e.g., processing unit 16, to be available for subsequent steps which determine reduced risk scores and in some instances to be available to access for subsequent presentation to the medical worker or patient when a recommendation is provided. The checking to find ancestor nodes may help reveal additional records stored in the medical record data structure which include relevant information about possible intervention options with respect to the chosen possible disease outcome.

For EXAMPLE A, in step 424 the patient data node graph 500 is checked whether the second patient data node 502*b* has any ancestor node and whether the sixth patient data node 502*f* has any ancestor node. The check will determine (1) that the first patient data node 502*a* representing the patient diagnosis of AMI of which STEMI is a sub-type is an ancestor node of the second patient data node 502*b* and (2) that the fourth patient data node 502*d* representing all ages is an ancestor node of the sixth patient data node 502*f* that represents the age range of 56 to 64 years old. Likewise, the check of step 424 of EXAMPLE A in the disease outcome relationship graph 600 indicates that the first disease outcome node 602*a* has no ancestor node.

As part of the step 424, the information regarding the identified ancestor nodes is taken back to the medical record data structure to find any additional entries, rows, or data segments that match with the identified ancestor nodes.

For EXAMPLE A, with the first patient data node 502*a* and the fourth patient data node 502*d* being identified as relevant ancestor nodes for the received patient data and for the patient from which the patient data was obtained, the medical record table 902 is searched with the first patient data node 502*a* and the fourth patient data node 502*d* as inputs for the search.

In EXAMPLE A, this search results in the first medical record table row 904 being identified as a match, because the first medical record table row 904 includes "502*a*" and "502*d*" as entries in its first and second columns regarding the patient data. The first medical record table row 904 also is a match because the outcome entry for its outcome column is "602*a*" which matches the EXAMPLE A chosen or inputted disease outcome of MACE. The inputted disease outcome may usually be chosen with the intent of finding the best intervention to avoid that disease outcome.

The second data row in the medical record table 902 is still not a match in EXAMPLE A, because even though the first column entry of "502*a*" for this second data row is a match to the information from one of the relevant ancestor nodes, the second column entry of "502*e*" for this second data row conflicts with the sixth patient data node 502*f*. The second column entry of "502*e*" corresponds to the fifth patient data node 502*e* which corresponds to the age range of less than or equal to 55 years age. That age range conflicts with the patient data in EXAMPLE A that the patient is 60 years old.

The third data row in the medical record table 902 was already identified in the initial matching (step 420) of EXAMPLE A as being a match with the patient data and with the selected possible disease outcome. The intervention information "708e" from this third data row was already used in step 422 to map in the intervention tree 700.

The fourth data row in the medical record table 902 is still not identified in EXAMPLE A as being a match, because the patient data entry of "502c" corresponding to a non-STEMI diagnosis still conflicts with the initial patient data of a STEMI diagnosis. This non-match is also apparent because neither of the entries in the first or second columns in the fourth data row is a direct match with the ancestor node that was found as newly relevant. In other words, neither of these entries ("502c", blank) is a direct match with the first patient data node 502a which is an ancestor node of the second patient data node 502b.

The fifth data row in the medical record table 902 would also be newly identified as a match for EXAMPLE A, because the fifth data row includes "502a" as an entry in its first column regarding the patient data. This entry "502a" is a direct match with the first patient data node 502a which was recognized as being an ancestor node to the second patient data node 502b which corresponds to the patient data of a STEMI diagnosis. This new match would also occur because the second column is blank and, therefore, has no entry that conflicts with the second patient data node 502b. This new match would also occur because the entry "602a" in the outcome column is a direct match to the first disease outcome node 602a that corresponds to the possible disease outcome of MACE for which an effective intervention is being searched.

Thus, the check for ancestor nodes of step 424 in EXAMPLE A revealed that the first medical record table row 904 and the fifth data row, in addition to the third data row, are matches for the patient data and for the chosen disease outcome.

Thus, as part of step 424 in EXAMPLE A the intervention option "708a" from the first medical table row 904 and the intervention option "708f" from the fifth data row would also be saved as referring to relevant intervention options for which information of their interventive effects is contained in the medical record data structure. A return to mapping in the intervention tree 700 would indicate that the first intervention node 708a that corresponds to a thrombolysis treatment corresponds to "708a" information and that the sixth intervention node 708f that corresponds to a primary CABG corresponds to the "708f" information. This information may also be stored, e.g., in memory 28, for reference when one or more recommendations are provided to the patient.

In step 426 of the process 400 shown in FIG. 4, the intervention tree, e.g., the intervention tree 700, is checked to determine all suitable combinations of the intervention options that were found. The same software or similar software described above that was used to perform the matching, the mapping, and the checking may also be used and programmed to perform the checking of step 426. Any suitable combination of intervention options that are determined may then be stored in a memory, e.g., in memory 28, connected to the processor, e.g., in processing unit 16, to be available for subsequent steps which determine reduced risk scores and in some instances to be available to access for subsequent presentation to the medical worker or patient when a recommendation is provided. The checking to determine suitable combinations may in some instances help reveal that the best treatment would include a combination of individual treatments or individual intervention measures or options.

For EXAMPLE A, the intervention tree 700 is checked in step 426 with regard to the identified intervention information of "708e", "708a", and "708f" to identify whether any of the intervention measures that correspond to this information may be suitably combined for a treatment plan for the patient to provide the best intervention to reduce the risk of incurring the negative disease outcome. The checking of the intervention tree 700 shows that the fifth and sixth intervention nodes 708e and 708f are both child nodes of an exclusive node 704a and, therefore, may not be suitably both given to a patient as a combination of treatments. Rather, a primary angioplasty or a primary CABG may be given to the patient but not both. The checking also indicates, however, that the thrombolysis treatment corresponding to the first intervention node 708a is a child node of a second inclusive node 708b and also is not a child node of the exclusive node 704a. Therefore, the thrombolysis treatment may be suitably combined with either the primary angioplasty or with the primary CABG as two separate treatment possibilities formed by a combination of individual intervention measures or individual intervention options. In shorthand, the two suitable combinations may be referred to as ("708a", "708e") and ("708a", "708f"). These two newly identified combinations may be stored in the memory, e.g., in memory 28, for use in a subsequent reduced risk score calculation that may be performed by a processor, e.g., processing unit 16.

In at least some embodiments, the steps 416 to 426 combined may together constitute a generation of one or more intervention options based on the patient data.

In step 427 of the process 400 shown in FIG. 4, a prompt may be given for more patient data to be provided from the patient, to allow a check for more matches of intervention options. Step 427 will be explained more in detail below with respect to Example D.

In step 428 of the process 400 shown in FIG. 4, for each of the found intervention options from steps 420, 424, 427 and for each of the suitable combinations found in step 426, a reduced risk score is determined. This determination may occur with the processor, e.g., processing unit 16, being programmed to include certain formulas which enable a reduced risk score to be calculated. This determination may also include checking the medical record data structure to obtain any risk score change information, such as a relative risk reduction amount for a particular intervention, that is stored in the medical record data structure. The reduction in the risk score may constitute an intervention effect of the respective intervention option, so determining the reduced risk score also helps analyze the intervention effect of that intervention option.

An absolute risk reduction (ARR) for a treatment or an intervention measure to reduce the possibility of an event happening to a group of people may be calculated by subtracting an absolute risk of a treatment group (ART) from an absolute risk of a control group (ARC). In other words, ARR can be calculated as an arithmetic difference of the ARs (e.g., ART from ARC) that happen in the treatment group and the control group. In other words, ARR=ARC−ART. In one example, if a risk of an event happening in the control group is 40% (ARC=40%) and a risk of the event happening in the treatment group is 30% (ART=30%), then the ARR for that treatment with respect to the particular event is calculated by 40%−30%=10% (or 0.10).

According to some embodiments of the disclosure, a value that is entitled a "relative risk reduction" (RRR) is employed to evaluate an effect of an intervention option and a reduced risk score. The relative risk reduction helps better characterize an intervention effect in the treatment group. The relative risk reduction (RRR) is the relative decrease in the risk of an adverse event in the treatment group compared to the control group. The relative risk reduction (RRR) is determined via RRR=(ARC−ART)/ARC=1−ART/ARC. In the above example where ARC=40% and ART=30%, the RRR for that treatment with respect to the particular event is calculated by 1-0.75=0.25.

For a specific intervention measure, the RRR of the intervention measure with respect to a given disease outcome can be collected from existing medical literature or studies. For example, there may be a study that shows that when certain patients take Aspirin regularly, their RRR is 0.25 with respect to cardiovascular death. Thus, taking the Aspirin reduces the possibility or chance that a patient would experience cardiovascular death.

For each of the one or more intervention options, an intervention effect may be evaluated by accounting for an influence of each of the one or more intervention measures of the corresponding intervention option on the risk score. According to one embodiment of the disclosure, accounting for the influence of each of the one or more intervention measures on the risk score may include computing the intervention effect by using a relative risk reduction of the corresponding intervention, with the relative risk reduction having been identified or determined from medical knowledge related to the corresponding intervention. According to one embodiment of the invention, the medical knowledge may be obtained from at least one medical literature or study whose information is stored in the medical record data structure. The intervention effect that is determined may be represented by a reduced risk score, with the lowest reduced risk score corresponding to the intervention with the greatest effect.

According to one embodiment of the disclosure, the reduced risk score q can be denoted as equation (2):

$$q=q(f(X),T) \quad (2)$$

where T is a vector of intervention measures of an intervention option, and f(x) represents the risk score r as discussed above. Here, equation (2) can be expanded as equation (3):

$$q(f(X), T) = f(X) * \prod_{i=1}^{n} (1 - RRR(t_i)) \quad (3)$$

where n is the number of intervention measures of an intervention option. RRR(t) is the relative risk reduction for an intervention option t.

As explained above, in EXAMPLE A five total intervention options were generated, namely those corresponding to the intervention information: "708e", "708a", "708f", ("708a", "708e"), and ("708a", "708f"), which include the three individual intervention options as well as the two suitable combinations. The medical record data table 902 shown in FIG. 9A shows that the medical study Estess (2002) concluded that the RRR for the "708a" intervention (Thrombolysis) is 0.31 (indicated in the first medical record table row 904), that the medical study Chucherat (2003) concluded that the RRR for the "708e" intervention (primary angioplasty) is 0.15 (indicated in the third data row), and that the medical study Yusuf (1994) concluded that the RRR for the "708f" intervention (primary CABG) is 0.39.

The formula (2) provided above may be used in EXAMPLE A to calculate the reduced risk score for each of the above-mentioned three individual interventions as well as for the two suitable combinations of intervention options. The calculations start from the risk score of 0.43 that was obtained in step 414 of EXAMPLE A.

TABLE 3

Example A

| Intervention option | RRR | Calculation starts from Risk Score of 0.43 | Reduced Risk Score (q) |
|---|---|---|---|
| 708a | 0.31 | 0.43*(1-0.31) | 0.297 |
| 708e | 0.15 | 0.43*(1-0.15) | 0.366 |
| 708f | 0.39 | 0.43*(1-0.39) | 0.262 |
| Combination: 708a, 708e | 0.31, 0.15 | 0.43*(1-0.31)*(1-0.15) | 0.252 |
| Combination: 708a, 708f | 0.31, 0.39 | 0.43*(1-0.31)*(1-0.39) | 0.181 |

These calculations show that data indicates that the combination of thrombolysis ("708a") and primary CABG ("708f") used together as interventions to the patient of EXAMPLE A would achieve the greatest reduction for the risk score, as the reduced risk score of 0.181 is smaller than each of the other four calculated reduced risk scores of EXAMPLE A. Thus, the combination of thrombolysis ("708a") and primary CABG ("708f") used together would have the greatest intervention effect of the five possible treatment options.

In an alternative example, namely in EXAMPLE D, the medical record table 902 shown in FIG. 9A was also created in step 402, MACE was also the disease outcome in step 412, and the patient data that was received included a diagnosis of a STEMI, like in EXAMPLE A. However, different from EXAMPLE A, in EXAMPLE D the patient data that was received in step 410 did not include any information about the age of the patient. When performing the step 416 in EXAMPLE D, the computer program would recognize that the second data row in medical record table 902 included a possible match for the patient, if the patient had an age of less than or equal to 55 years old. Specifically, the second data row in the medical record table 902 includes an entry of "502e" in the "P: extended" column, and that "502e" entry corresponds to the fifth patient data node 502e that is shown in the patient data node graph 500 of FIG. 5. The fifth patient data node 502e corresponds to an age that is less than or equal to 55 years old.

In this situation in EXAMPLE D where a possible but unconfirmed row match is identified, a prompt to the doctor, the medical worker, or the patient may be generated, prompting them to enter in the age of the patient so that the computer program can determine if the second data row is a match for the patient and if it, therefore, would contain useful quantitative data to help with developing a health plan for the patient. This prompting is an example of step 427 in process 400. This prompting may occur by the generation of a graphical user interface prompt that is displayed, e.g., on display 24, or by the generation of an audio question. For example, if the computer program performed the prompting and the patient or medical worker then entered in an age of 48 years old for the patient, the computer program may then determine that the second data row is a match for the patient. Thus, different from EXAMPLE A, in EXAMPLE D four individual options would be found. Then using the check for suitable combinations in step 426 in the intervention tree 700, suitable combinations of intervention options were determined in EXAMPLE D. This step 426 for EXAMPLE D would produce a total of seven possible combinations in addition to the four individual intervention options. The suitable combinations set of the seven combinations in EXAMPLE C provided below are the same combination of intervention numbers as the seven suitable combinations for EXAMPLE D.

For EXAMPLE B that was introduced earlier, the obtaining in step 414 of the risk score for MACE was 0.249 for a patient who is 89 years old, who has a white blood count of 12*10○9/L, and who has a Killip level of 3. Further in Example B, the medical record data structure includes entries which indicate that the following eight interventions would have a relative risk reduction value as indicated in the Table 4 that is provided below. These relative risk reduction values came from medical literature whose information was entered into the medical record data structure in another step of the process 400, for example in step 402 of the process.

TABLE 4

Example B

| | T-interventions | RRR(t) |
|---|---|---|
| 1 | primary PCI | 0.32 |
| 2 | Thrombolysis | 0.31 |
| 3 | ACEI ARB | 0.07 |
| 4 | Aspirin | 0.15 |
| 5 | Clopidogrel | 0.07 |
| 6 | Ticagrelor | 0.12 |
| 7 | Metoprolol | 0.36 |
| 8 | high dosage statin | 0.35 |

The steps 416 to 424 of process 400 performed in EXAMPLE B resulted in interventions 1, 5, and 6 being generated as intervention options for the 89-year-old patient. The step 426 also indicated that the combinations of interventions (1, 5) and (1, 6) would also be suitable for this 89-year-old patient. Using these five intervention options (three individual interventions plus two combinations) and recalling that the risk score was 0.249, step 428 for EXAMPLE B determines the following reduced risk scores for the interventions and the suitable combinations of interventions as indicated in Table 5 provided below:

TABLE 5

Example B

| f(x) | primary PCI | Thromb. | ACEI ARB | Aspir. | Clopidogrel | Ticagrelor | Metoprolol | high dosage statin | q(f(x), T) reduced risk score |
|---|---|---|---|---|---|---|---|---|---|
| 0.249 | + | | | | | | | | 0.249 * (1 − 0.32) = 0.169 |
| 0.249 | | | | | + | | | | 0.249 * (1 − 0.07) = 0.232 |
| 0.249 | | | | | | + | | | 0.249 * (1 − 0.12) = 0.219 |
| 0.249 | + | | | | + | | | | 0.249 * (1 − 0.32) * (1 − 0.07) = 0.157 |
| 0.249 | + | | | | | + | | | 0.249 * (1 − 0.32) * (1 − 0.12) = 0.149 |

These calculations show that data indicates that the combination of primary PCI and ticagrelor used together as interventions to the 89-year-old patient of EXAMPLE B would achieve the greatest reduction for the risk score and the greatest intervention effect, as the reduced risk score of 0.149 is smaller than each of the other four calculated reduced risk scores of EXAMPLE B.

A further EXAMPLE C is provided below to further illustrate the features of step 428 of determining the risk score for the intervention options. In EXAMPLE C, four intervention options I1, I2, I5, and I6 were generated in steps 416 to 424 of the process 400. The medical record data structure for this EXAMPLE C included the following RRR information provided from medical literature pieces L1, L2, L3, and L4, respectively. This RRR information is provided in Table 6 below, for each of the four individual intervention measures or options.

TABLE 6

EXAMPLE C

| Intervention options | RRR | Literature |
|---|---|---|
| I1 | 0.1 | L1 |
| I2 | 0.2 | L2 |
| I5 | 0.25 | L3 |
| I6 | 0.3 | L4 |

The step 426 in EXAMPLE C indicated that it is not suitable to combine intervention options I5 and I6 with each other, but that all other combinations of the four intervention options were suitable. For EXAMPLE C, the risk score from step 414 was obtained as being 0.5 for patient disease outcome H. Using the intervention options and starting from the risk score of 0.5, step 428 for EXAMPLE C determines the following reduced risk scores for the individual intervention options and the suitable combinations of interventions as indicated in Table 7 provided below:

TABLE 7

Example C

| Intervention option | Calculation starting from Risk Score of 0.5 | Reduced Risk Score (q) |
|---|---|---|
| I1 | 0.5*(1−0.1) | 0.45 |
| I2 | 0.5*(1−0.2) | 0.4 |
| I5 | 0.5*(1−0.25) | 0.38 |

TABLE 7-continued

Example C

| Intervention option | Calculation starting from Risk Score of 0.5 | Reduced Risk Score (q) |
|---|---|---|
| I6 | 0.5*(1−0.3) | 0.35 |
| I1, I2 | 0.5*(1−0.1)*(1−0.2) | 0.36 |

TABLE 7-continued

Example C

| Intervention option | Calculation starting from Risk Score of 0.5 | Reduced Risk Score (q) |
|---|---|---|
| I1, I5 | 0.5*(1-0.1)*(1-0.25) | 0.34 |
| I1, I6 | 0.5*(1-0.1)*(1-0.3) | 0.32 |
| I2, I5 | 0.5*(1-0.2)*(1-0.25) | 0.3 |
| I2, I6 | 0.5*(1-0.2)*(1-0.3) | 0.28 |
| I1, I2, I5 | 0.5*(1-0.1)*(1-0.2)*(1-0.25) | 0.27 |
| I1, I2, I6 | 0.5*(1-0.1)*(1-0.2)*(1-0.3) | 0.25 |

These calculations show that data indicates that the combination of intervention options I1, I2, and I6 used together as interventions to the patient of EXAMPLE C would achieve the greatest reduction for the risk score and the greatest intervention effect, as the reduced risk score of 0.25 is smaller than each of the other ten calculated reduced risk scores of EXAMPLE C.

In some embodiments of the disclosure, the medical record data structure may have entries from more than one piece of literature or study that gives information or data about effectiveness of a particular intervention option, e.g. more than one study may provide a unique RRR for one single intervention option. According to this embodiment, the medical knowledge may be obtained from a plurality of pieced of literature or from a plurality of studies. Each of the plurality of pieces of literature or studies may be assigned with a respective weight or variance when computing the reduced risk reduction. More weight may be assigned to the piece of literature which has shown the intervention option as achieving a more precise effect.

According to some embodiments of the disclosure, the weight of each literature or study may be preset by considering its accuracy, journal impact factor, peer review, or number of references it cites or number of times it is cited by other articles/studies. According to another embodiment of the disclosure, the weight of each piece of literature or study may be determined by using the DerSimonian and Laird method (D-L method) that considers the between-studies variance of the observed effect. In a further embodiment, methods other than the D-L method known to those skilled in the art can be also used to determine the weight of each literature or study.

Thus, in these embodiments the step 428 may also include assigning a respective weight or variance to each of the plurality of pieces of literature or studies when computing the reduced risk scores or determining the intervention effect. For example, for an intervention of quitting smoking, three different pieces of medical literature L1, L2, and L3 may provide a unique RRR value for reducing the risk that a patient or patient group will experience an outcome of "O". Table 8 provided below illustrates these weights and unique RRR values for L1, L2, and L3.

TABLE 8

Example E

| Literature | Weight | RRR |
|---|---|---|
| L1 | 0.8 | 0.35 |
| L2 | 0.5 | 0.42 |
| L3 | 0.6 | 0.40 |

For these embodiments which include weighting of different pieces of literature, RRR(t) from equation (3) provided above can be represented as equation (4) below:

$$RRR(t) = \frac{\sum_{k=1}^{m} w_k * rrr(t)}{\sum_{k=1}^{m} w_k} \quad (4)$$

where m is the number of pieces of literature or studies that can be leveraged for one intervention, and where w is the weight of the importance of the corresponding literature or study.

Then, according the above equation (4), in EXAMPLE E using the information from Table 8 above the combined effect RRR={(0.8*0.35)+(0.5*0.42)+(0.6*0.40)}/(0.8+0.5+0.6) 0.38. Thus, the computed value of "0.38" will be recorded as the final RRR of the intervention measure "quitting smoking" according to the three pieces of literature L1 to L3. The weights from Table 8 provided above may be obtained using the D-L method.

An example of calculating a weight using D-L method is described now as EXAMPLE F. In this example, both study 1 and study 2 in the medical record data structure provide a relative risk reduction for using high dosages of statin to reduce the risk of MACE. In this study, both studies are given the same weight, but the studies have provided a different variance of the observed effect size about its true effect. Study 1 provided an rrr=0.42, but a variance $v_1$=0.39. Study 2 provided an rrr=0.35, but a variance $v_2$=0.1. Because the relative risk reduction values between the two studies will be combined, the relative risk reduction value for one study will be referred to as "rrr" and the combined relative risk reduction value will be referred to as "RRR".

For the calculations, RRR(t) is the combined relative risk reduction of the high dosages of statin determined for both studies. "k" is the number of studies in the analysis. $W_i$ is the weight assigned to each study. $Y_1$ is the observed effect in study i. $V_i$ is the variance of $Y_i$ about its true effect. $T^2$ is the between-studies variance.

TABLE 9

Example F

| | |
|---|---|
| $C = \sum_{i=1}^{k} w_i - \frac{\sum_{i=1}^{k} w_i^2}{\sum_{i=1}^{k} w_i}$ | k = 2. $w_i$ = 1, due to both studies being weighted equally C = 1 |
| df = k - 1 | df = 1 |
| $\overline{Y}_w = \frac{\sum_{i=1}^{k} w_i Y_i}{\sum_{i=1}^{k} w_i}$ | $\overline{Y}_w$ = 0.385 |
| $Q = \sum_{i=1}^{k} w_i (Y_i - \overline{Y}_w)^2$ | Q = 0.00245 |
| $T^2 = \max\left\{0, \frac{Q - df}{C}\right\}$ | $T^2$ = 0 |
| $W_i = \frac{1}{V_i + T^2}$ | $W_1$ = 2.564, $W_2$ = 10 |
| $RRR(t) = \frac{\sum_{i=1}^{k} w_i rrr(t)}{\sum_{i=1}^{k} w_i}$ | (2.564 * 0.42 + 10 * 0.35)/(2.564 + 10) = 0.364 |

Thus, these calculations indicate that, in this EXAMPLE F with studies 1 and 2, the relative risk reduction saved for the high dosage statin treatment will be recorded as 0.364.

In step 430 of the process 400 shown in FIG. 4, the reduced risk scores that were determined in step 428 are compared with each other. The same software or similar software described above that was used to perform the matching and mapping may also be used to perform the comparing of step 430. The comparing will clarify which intervention or which combination of interventions had the greatest intervention effect and which achieved the lowest reduced risk score. The comparing may include ranking the interventions and the combinations of interventions in an ascending or a descending order according to the reduced risk scores.

In step 432 of the process 400 shown in FIG. 4, a recommendation of one or more of the found intervention options or of one or more of the combinations of intervention options is provided. This providing may be performed via the computer program displaying a message on a display screen, e.g., on display 24, or via the computer program transmitting via a speaker connected to the computer an audio message with a recommendation. In some embodiments, the computer program will recommend the intervention or the combination of interventions that had the greatest intervention effect and which achieved the lowest reduced risk score. The providing of the recommendation may constitute a treatment decision being made.

This recommendation in step 432 may be performed via the computer program listing or displaying or announcing the interventions and the combinations in an ascending or a descending order according to the reduced risk scores and highlighting the lowest-positioned or the highest-positioned entry. The highlighted entry would constitute the recommend intervention. In some embodiments, when multiple intervention options have a similar intervention effect, e.g., produce a similarly reduced risk score, then the computer program may recommend multiple intervention options while providing information regarding the various effects. For example, multiple entries could be highlighted or announced as being similarly superior over the other interventions with respect to their intervention effects or reduced risk scores, and each of the multiple entries may be highlighted with a different color on the display screen or with different background noises or music via the speaker. As part of step 430, an intervention or a combination with the smallest q resulting from equation (2) may be recommended.

In EXAMPLE A, as part of step 432 the computer program may recommend that the patient receive the combination of interventions of thrombolysis ("708a") and primary CABG ("708f"), because this combination had the greatest intervention effect and produced the lowest reduced risk score, namely with the reduced risk score being 0.181. In EXAMPLE B, as part of step 432 the computer program may recommend that the patient receive the combination of primary PCI and ticagrelor, because this combination had the greatest intervention effect and achieved the lowest reduced risk score, with the reduced risk score being 0.149. In EXAMPLE C, as part of step 432 the computer program may provide a recommendation that the patient receive the combination of intervention options I1, I2, and I6, because this combination had the greatest intervention effect and achieved the lowest reduced risk score, namely a risk of 0.25.

In step 434 of the process 400 shown in FIG. 4, the computer program checks whether new medical records, studies, or literature have been made available or published which provide new disease risk quantitative information and which provide intervention effect quantitative information. This checking may be performed in the same manner that step 402 is performed, with either a worker manually checking newly published medical pieces or the computer program scanning the internet or scanning medical studies and/or pieces of medical literature that are uploaded into the program, and using NLP techniques to identify medical literature with quantitative information.

In step 436 of the process 400 shown in FIG. 4, if the check in step 434 indicates that one or more new medical studies or literature with quantitative information is available, the computer program adds the information from the new medical studies or literature into the medical record data structure, into the patient data node graph 500, into the disease outcome relationship graph 600, and/or into the intervention tree 700. This addition may be performed with either a worker manually typing or entering in the information from the newly published and identified medical studies or literature or with the computer program harvesting the information from the pieces of medical literature or studies and creating new entries in the medical record data structure, the patient data node graph 500, the disease outcome relationship graph 600, and/or the intervention tree 700.

Examples of step 436 for EXAMPLE A are described below with respect to FIGS. 8 and 9B. For example, in step 434 a piece of literature, Hjalmarson 1981, is newly found which shows that the risk of mortality can be reduced by 0.36 if metoprolol is used as an intervention. FIG. 9B shows a situation where a new record entry row 908 is added to the medical record table 902 to create an updated medical record table 906, with the new record entry row 908 including the information from the Hjalmarson, 1981 article and including an entry "712" in the Outcome column that is labeled "O".

Figure 8:
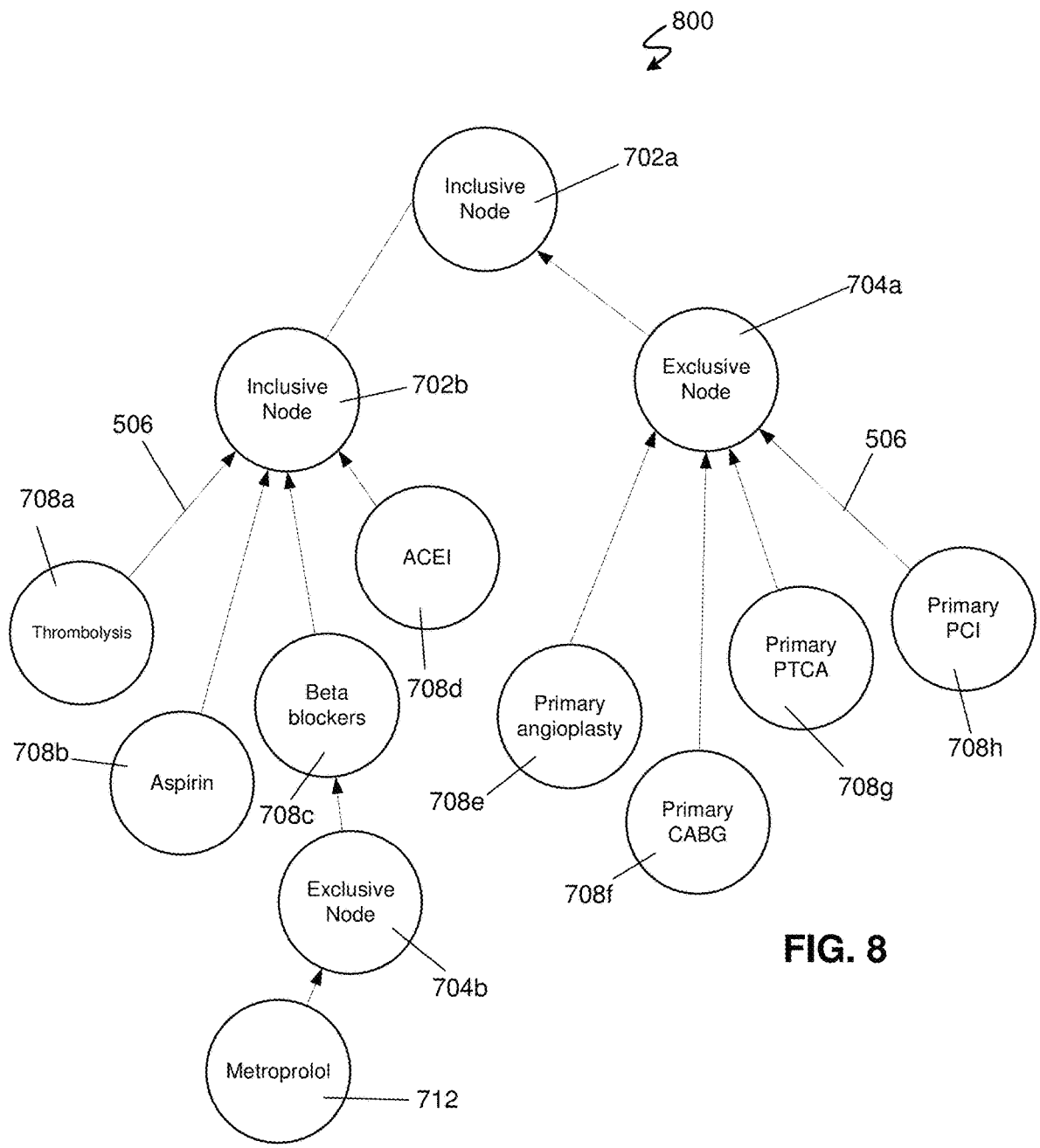
FIG. 8 shows a modified intervention tree as compared to the intervention tree shown in FIG. 7.
Figure 9B:
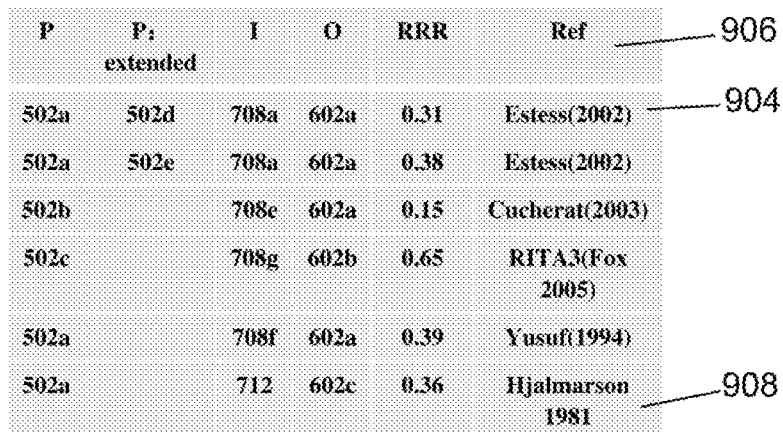
FIG. 9B shows a modified medical record data structure as compared to the medical record data structure shown in FIG. 9A.

FIG. 8 shows an updated intervention tree 800 that is formed by modifying the intervention tree 700 by a second exclusive node 704 being added that is connected to the third intervention node 708c and by adding a new intervention node 712 that is connected to the second exclusive node 704b. The Hjalmarson article included data indicating that intervention of metoprolol can be used in a patient who experienced an AMI (corresponding to the first patient data node 502a) to reduce risk of mortality (corresponding to the third disease outcome node 602c) by 0.36. Thus, in the updated medical record table 906 an entry of "602c" is entered into the Outcome column "O" of the new record entry row 908 and an entry of "502a" is entered into the Patient Data column "P". The Hjalmarson article indicated that metoprolol is a Beta blocker (corresponding to third intervention node 702c) and cannot be used as a treatment in combination with other Beta blockers. FIG. 8 shows, therefore, that the new intervention node 712 is connected to the third invention node 702c via the second exclusive node 704b.

In step 438 of the process 400 shown in FIG. 4, the computer program may check whether an evaluation of disease risk reduction should be performed for another patient. If the step 438 indicates an affirmative, then the process can return to step 410 to repeat step 410 but with respect to the new patient. Steps 402-408 do not need to be repeated, because the medical record data structure created in step 402, the patient data node graph 500 created in step 404, the disease outcome relationship graph 600 created in step 406, and the intervention tree 700 that was created in step 408 (or the updated intervention tree 800 that may have been created in step 436) may be used for the disease risk reduction evaluation with respect to the new patient. With the check for a new patient in step 438, the process 400 may delay until a later time when a new patient interacts to request an evaluation or when the same patient interacts to request another evaluation. Then, the process 400 may begin with step 410 because the medical record data structure, the patient data node graph 500, the disease outcome relationship graph 600, and the intervention tree 700 or the updated intervention tree 800 may be used for the disease risk reduction evaluation with respect to the new patient.

The method, computer system, and computer program product described herein help medical workers leverage values determined in medical research to improve medical treatment selection, to improve the automation of medical treatment evaluation, and to remove the need for researchers and medical care workers to perform redundant medically-controlled experiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
generating, by one or more processors, a medical record data structure via automated internet scanning implementing natural language processing, the medical record data structure comprising record groups, each record group comprising a set of linked medical record data including medical patient data and at least one intervention option;
storing, by the one or more processors, the generated medical record data structure in a computer memory;
receiving, by the one or more processors, patient data of a patient;
receiving, by the one or more processors, a selection of a disease outcome;
determining, by the one or more processors, a risk score that the patient will experience the selected disease outcome, wherein the determining uses the patient data;
generating, by the one or more processors, intervention options based on the patient data and by accessing the medical record data structure stored in the computer memory, wherein the generating is performed automatically via the one or more processors running disease risk reduction evaluation software and comprises:
matching, by the one or more processors, the patient data and the selected disease outcome with record groups in the medical record data structure,
matching, by the one or more processors, the matched record groups with respective nodes of at least one medical record data graph, the at least one medical record data graph representing relationships amongst medical record data and comprising interconnected medical record data nodes,
locating, by the one or more processors, at least one ancestor node of a matched node, and
using, by the one or more processors, the located at least one ancestor node to identify at least one additional intervention option of the intervention options;
determining, by the one or more processors, an intervention effect for each of the intervention options including the at least one additional intervention option, wherein the intervention effect changes the risk score;
comparing, by the one or more processors, the intervention effects; and
providing, by the one or more processors, a recommendation of at least one of the intervention options based on the comparing of the intervention effects.

2. The computer-implemented method according to claim 1, wherein the intervention effects are determined by determining a relative risk reduction of a corresponding intervention option of the intervention options based on medical knowledge related to the corresponding intervention option.

3. The computer-implemented method according to claim 2, wherein the medical knowledge is obtained from a plurality of pieces of literature or from a plurality of studies; and
wherein each of the plurality of pieces of literature or each of the studies is assigned a respective weight or variance when the intervention effect is determined.

4. The computer-implemented method according to claim 1, wherein
the record groups in the medical record data structure comprise linked entries storing a specific population information relative to at least one member selected from the group consisting of recorded patient data, a given disease outcome, an intervention option, and a corresponding relative risk reduction.

5. A computer system for evaluation of reduction of disease risk, the system comprising:
one or more processors;
a memory coupled to at least one of the one or more processors; and
a set of computer program instructions stored in the memory and executed by at least one of the one or more processors in order to perform a method comprising:
generating a medical record data structure via automated internet scanning implementing natural language processing, the medical record data structure comprising record groups, each record group comprising a set of linked medical record data including medical patient data and at least one intervention option;
storing the generated medical record data structure in a computer memory;
receiving patient data of a patient;
receiving a selection of a disease outcome;
determining a risk score that the patient will experience the selected disease outcome, wherein the determining uses the patient data;
generating intervention options based on the patient data and by accessing the medical record data structure stored in the computer memory, wherein the generating is performed automatically and comprises:
matching the patient data and the selected disease outcome with record groups in the medical record data structure,
matching the matched record groups with respective nodes of at least one medical record data graph, the at least one medical record data graph representing relationships amongst medical record data and comprising interconnected medical record data nodes,
locating at least one ancestor node of a matched node, and using the located at least one ancestor node to identify at least one additional intervention option of the intervention options;

determining an intervention effect for each of the intervention options including the at least one additional intervention option, wherein the intervention effect changes the risk score;

comparing the intervention effects; and providing a recommendation of at least one of the intervention options based on the comparing of the intervention effects.

6. The computer system according to claim 5, wherein the intervention effects are determined by determining a relative risk reduction of a corresponding intervention option of the intervention options based on medical knowledge related to the corresponding intervention option.

7. The computer system according to claim 6, wherein the medical knowledge is obtained from a plurality of pieces of literature or from a plurality of studies; and wherein each of the plurality of pieces of literature or each of the studies is assigned a respective weight or variance when the intervention effect is determined.

8. The computer system according to claim 5, wherein the record groups in the medical record data structure comprise linked entries storing a specific population information relative to at least one member selected from the group consisting of recorded patient data, a given disease outcome, an intervention option, and a corresponding relative risk reduction.

9. A computer program product for evaluation of reduction of disease risk, the computer program product comprising a computer readable storage medium having program instructions embodied therewith, wherein the program instructions are executable by a processor to cause the processor to perform a method comprising:

generating a medical record data structure via automated internet scanning implementing natural language processing, the medical record data structure comprising record groups, each record group comprising a set of linked medical record data including medical patient data and at least one intervention option;

storing the generated medical record data structure in a computer memory;

receiving patient data of a patient;

receiving a selection of a disease outcome;

determining a risk score that the patient will experience the selected disease outcome, wherein the determining uses the patient data;

generating intervention options based on the patient data and by accessing the medical record data structure stored in the computer memory, wherein the generating is performed automatically and comprises:

matching the patient data and the selected disease outcome with record groups in the medical record data structure, matching the matched record groups with respective nodes of at least one medical record data graph, the at least one medical record data graph representing relationships amongst medical record data and comprising interconnected medical record data nodes, locating at least one ancestor node of a matched node, and using the located at least one ancestor node to identify at least one additional intervention option of the intervention options;

determining an intervention effect for each of the intervention options including the at least one additional intervention option, wherein the intervention effect changes the risk score;

comparing the intervention effects; and providing a recommendation of at least one of the intervention options based on the comparing of the intervention effects.

10. The computer program product according to claim 9, wherein the intervention effects are determined by determining a relative risk reduction of a corresponding intervention option of the intervention options based on medical knowledge related to the corresponding intervention option.

11. The computer program product according to claim 10, wherein the medical knowledge is obtained from a plurality of pieces of literature or from a plurality of studies; and wherein each of the plurality of pieces of literature or each of the studies is assigned a respective weight or variance when the intervention effect is determined.

12. The computer program product according to claim 9, wherein the record groups of the medical record data structure comprise linked entries storing a specific population information relative to at least one member selected from the group consisting of recorded patient data, a given disease outcome, an intervention option, and a corresponding relative risk reduction.

13. A computer-implemented method comprising:

generating, by one or more processors, a medical record data structure via automated internet scanning implementing natural language processing, the medical record data structure comprising record groups, each record group comprising a set of linked medical record data including medical patient data and at least one intervention option;

storing, by the one or more processors, the generated medical record data structure in a computer memory;

receiving, by the one or more processors, patient data of a patient;

receiving, by the one or more processors, a selection of a disease outcome;

determining, by the one or more processors, a risk score that the patient will experience the selected disease outcome, wherein the determining uses the patient data;

generating, by the one or more processors, intervention options based on the patient data and by accessing the medical record data structure stored in the computer memory, wherein the intervention options comprise individual intervention options and at least one combination of intervention options and the generating is performed automatically via the one or more processors running disease risk reduction evaluation software and comprises:

matching, by the one or more processors, the patient data and the selected disease outcome with record groups in the medical record data structure to determine the individual intervention options, matching, by the one or more processors, the matched record groups with respective nodes of at least one medical record data graph, the at least one medical record data graph representing relationships amongst medical record data and comprising interconnected medical record data nodes, locating, by the one or more processors, at least one ancestor node of a matched node in the at least one medical record data graph, using, by the one or more processors, the located at least one ancestor node to identify at least one additional intervention option of the intervention options, and checking, by the one or more processors, an intervention tree to determine the at least one combination of intervention options, the intervention tree comprising intervention option nodes and defining relationships among multiple intervention options, the checking the intervention tree comprising locating at least one ancestor node of a node representing a determined individual intervention option;

determining, by the one or more processors, a reduced risk score achieved by each of the intervention options with respect to the selected disease outcome;

comparing, by the one or more processors, the reduced risk scores; and providing, by the one or more processors, a recommendation of at least one of the intervention options based on the comparing of the reduced risk scores.

14. The computer-implemented method according to claim 13, further comprising:
obtaining a piece of literature or a study containing quantitative information with respect to medical knowledge; and
updating the medical record data structure by adding an entry corresponding to the obtained piece of literature or study.

15. The computer-implemented method according to claim 13, wherein the patient data includes at least one member selected from the group consisting of: demographic data, a vital sign, a lab test result, and a diagnostic result.

16. The computer-implemented method according to claim 13, wherein the at least one medical record data graph comprises a patient data node graph and a disease outcome relationship graph.

17. A computer system for evaluation of reduction of disease risk, the computer system comprising:
one or more processors;
a memory coupled to at least one of the one or more processors; and
a set of computer program instructions stored in the memory and executed by at least one of the one or more processors in order to perform a method comprising:
generating a medical record data structure via automated internet scanning implementing natural language processing, the medical record data structure comprising record groups, each record group comprising a set of linked medical record data including medical patient data and at least one intervention option;
storing the generated medical record data structure in the memory;
receiving patient data of a patient;
receiving a selection of a disease outcome;
determining a risk score that the patient will experience the selected disease outcome, wherein the determining uses the patient data;
generating intervention options based on the patient data and by accessing the medical record data structure stored in the memory, wherein the intervention options comprise individual intervention options and at least one combination of intervention options and the generating comprises:

matching the patient data and the selected disease outcome with record groups in the medical record data structure to determine the individual intervention options, matching the matched record groups with respective nodes of at least one medical record data graph, the at least one medical record data graph representing relationships amongst medical record data and comprising interconnected medical record data nodes, locating at least one ancestor node of a matched node in the at least one medical record data graph, using the located at least one ancestor node to identify at least one additional intervention option of the intervention options, and checking an intervention tree to determine the at least one combination of intervention options, the intervention tree comprising intervention option nodes and defining relationships among multiple intervention options, the checking the intervention tree comprising locating at least one ancestor node of a node representing a determined individual intervention option;

determining a reduced risk score achieved by each of the intervention options with respect to the selected disease outcome;

comparing the reduced risk scores; and providing a recommendation of at least one of the intervention options based on the comparing of the reduced risk scores.

18. The computer system of claim 17, wherein the method further comprises:
obtaining a piece of literature or a study containing quantitative information with respect to medical knowledge; and
updating the medical record data structure by adding an entry corresponding to the obtained piece of literature or study.

19. The computer system of claim 17, wherein the patient data includes at least one member selected from the group consisting of: demographic data, a vital sign, a lab test result, and a diagnostic result.

20. The computer system of claim 17, wherein the at least one medical record data graph comprises a patient data node graph and a disease outcome relationship graph.

21. The method of claim 1, wherein the at least one medical record data graph is selected from a group consisting of a patient data node graph and a disease outcome relationship graph.

22. The method of claim 1, wherein the at least one medical record data graph comprises a patient data node graph that represents relationships of multiple types of patient data.

23. The method of claim 22, further comprising generating, by the one or more processors, the patient data node graph via automated internet scanning implementing natural language processing.

24. The method of claim 1, wherein each record group comprises entries selected from a group consisting of patient data, an intervention option, a possible disease outcome, a relative risk reduction, and a medical data source name.

25. The method of claim 1, wherein the medical record data structure comprises at least one link to the nodes of the at least one medical record data graph.

* * * * *